(12) United States Patent
Vetter et al.

(10) Patent No.: US 9,259,211 B2
(45) Date of Patent: Feb. 16, 2016

(54) AUTOMATED, SELECTABLE, SOFT TISSUE EXCISION BIOPSY DEVICES AND METHODS

(71) Applicant: TRANSMED7, LLC, Portola Valley, CA (US)

(72) Inventors: Eugene H Vetter, Portola Valley, CA (US); James W Vetter, Portola Valley, CA (US); Alisen E Vetter, Shoreview, MN (US)

(73) Assignee: TRANSMED7, LLC, Portola Valley, CA (US)

( * ) Notice: Subject to any disclaimer, the term of this patent is extended or adjusted under 35 U.S.C. 154(b) by 0 days.

(21) Appl. No.: 13/935,422

(22) Filed: Jul. 3, 2013

(65) Prior Publication Data

US 2014/0180302 A1 Jun. 26, 2014

Related U.S. Application Data

(60) Provisional application No. 61/745,696, filed on Dec. 24, 2012.

(51) Int. Cl.
| | |
|---|---|
| *A61B 10/00* | (2006.01) |
| *A61B 10/02* | (2006.01) |
| *A61B 17/3205* | (2006.01) |
| *A61B 17/32* | (2006.01) |
| *A61B 18/14* | (2006.01) |

(52) U.S. Cl.
CPC ............ *A61B 10/0266* (2013.01); *A61B 10/025* (2013.01); *A61B 10/0283* (2013.01); *A61B 17/3205* (2013.01); *A61B 17/320016* (2013.01); *A61B 17/32056* (2013.01); *A61B 18/149* (2013.01); *A61B 2010/0208* (2013.01)

(58) Field of Classification Search
CPC .................................................. A61B 10/0266
USPC .................................................. 600/562–568
See application file for complete search history.

(56) References Cited

U.S. PATENT DOCUMENTS

| | | | |
|---|---|---|---|
| 4,202,338 | A | 5/1980 | Bitrolf |
| 4,611,594 | A | 9/1986 | Grayhack et al. |
| 5,197,968 | A | 3/1993 | Clement et al. |
| 5,611,803 | A | 3/1997 | Heaven |
| 6,514,248 | B1 | 2/2003 | Eggers |

(Continued)

OTHER PUBLICATIONS

USPTO Office Action of Sep. 15, 2014 in related U.S. Appl. No. 14/311,279.

(Continued)

*Primary Examiner* — Brian Szmal
*Assistant Examiner* — H. Q. Nguyen
(74) *Attorney, Agent, or Firm* — Young Law Firm, P.C.

(57) ABSTRACT

An excisional biopsy and delivery device may comprise one or more rotating, penetrating and cutting rod elements. The rod elements may be configured to advance from a stored and confined first position and rotate about an axis, while being simultaneously revolved about a central axis. The rod elements may then assume a second released and expanded configuration that is operative to cut around and surround target tissue. In this manner, the rod elements are operative to move through the surrounding tissue to create a volume of revolution and to sever and capture the target tissue contained within the volume of revolution from the surrounding tissue. The severed and captured volume of revolution containing the target tissue may then be removed.

15 Claims, 18 Drawing Sheets

(56) References Cited

U.S. PATENT DOCUMENTS

| | | |
|---|---|---|
| 6,540,695 B1 | 4/2003 | Burbank et al. |
| 6,626,903 B2 | 9/2003 | McGuckin et al. |
| 6,855,140 B2 | 2/2005 | Albrecht |
| 7,322,938 B2 | 1/2008 | Burbank et al. |
| 7,468,042 B2 | 12/2008 | Kim |
| 7,753,920 B2 | 7/2010 | McGuckin |
| 7,846,108 B2 | 12/2010 | Kim |
| 2001/0047169 A1 | 11/2001 | McGuckin et al. |
| 2002/0026188 A1 | 2/2002 | Balbierz |
| 2003/0114773 A1 | 6/2003 | Janssens |
| 2005/0182339 A1 | 8/2005 | Chernomorsky et al. |
| 2006/0224082 A1* | 10/2006 | Vetter et al. .................. 600/564 |
| 2009/0269774 A1 | 10/2009 | Rothenberg et al. |
| 2010/0152609 A1 | 6/2010 | Zwolinski et al. |

OTHER PUBLICATIONS

USPTO Office Action of Jun. 18, 2014 in related U.S. Appl. No. 13/935,416.

International Search Report and Written Opinion of the International Searching Authority mailed Jan. 16, 2014 in related PCT application PCT/US13/68989 of Jul. 11, 2013.

* cited by examiner

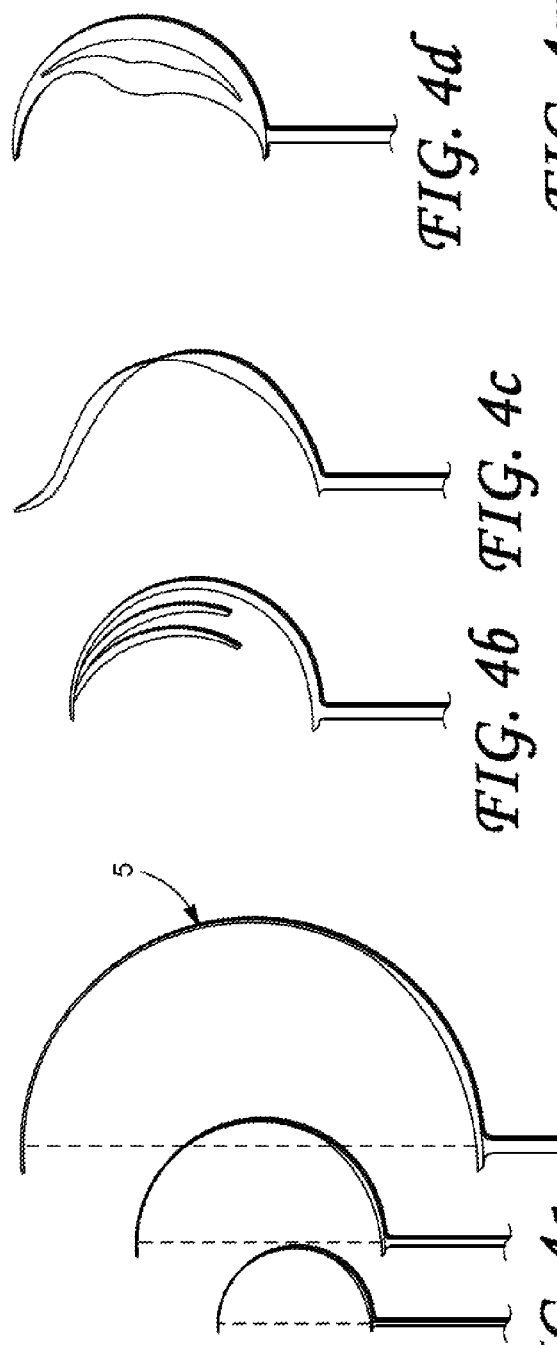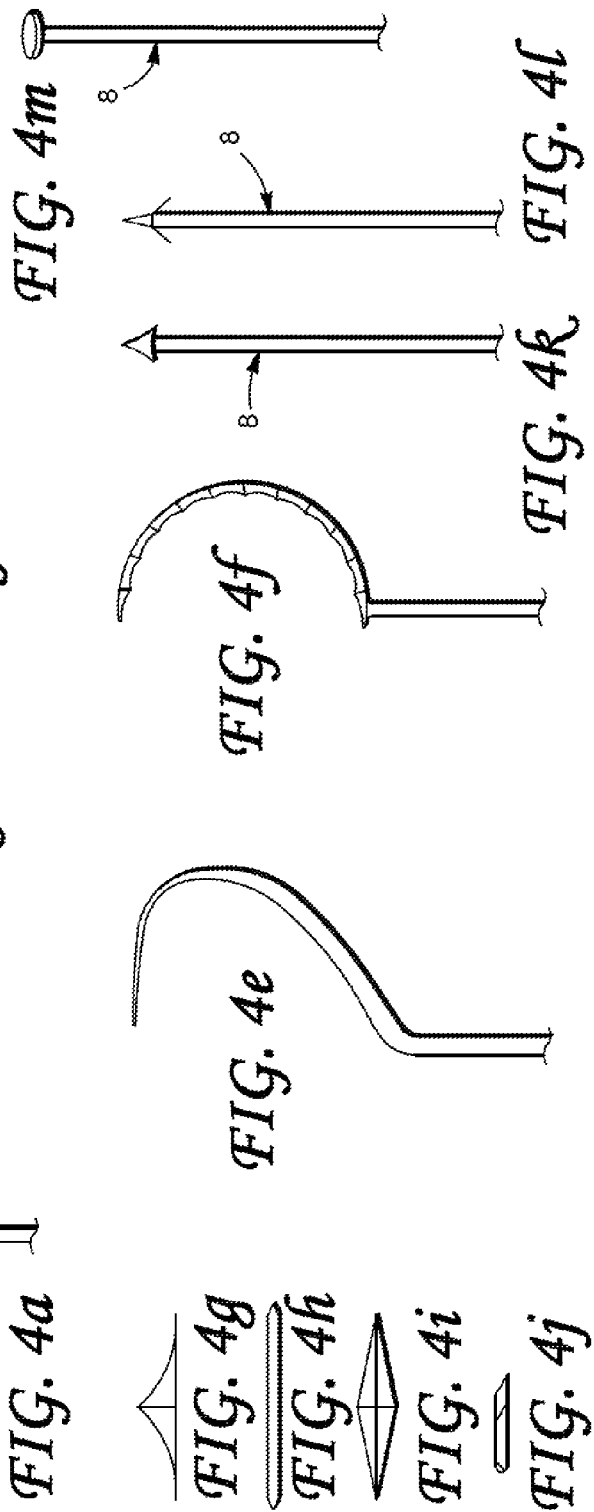

AUTOMATED, SELECTABLE, SOFT TISSUE EXCISION BIOPSY DEVICES AND METHODS

BACKGROUND

Embodiments are in the technical field of medical devices and methods. More particularly, embodiments are in the technical field of image guided soft tissue surgical diagnostic and therapeutic procedures, including devices for capture, immobilization, isolation, excision and retrieval of any tissue that is surrounded by soft tissue or foreign bodies surrounded by soft tissue, and corresponding methods for capturing, immobilizing, isolating, excision of; and retrieving any tissue or foreign bodies surrounded by soft tissue.

SUMMARY

Embodiments are drawn to various medical and surgical devices and methods that may be used for excision procedures, including the capture, immobilization, isolation, excision (resection) and retrieval of normal-appearing and/or abnormal-appearing tissues surrounded by soft tissue or foreign bodies surrounded by soft tissue. Embodiments also include devices and methods for intra-procedure or subsequent shaping of the cavity from which the target tissue or foreign body is excised, thereby enabling optimal subsequent post-procedure methods. Embodiments may also be configured to capture, immobilize, isolate and provide treatment or materials to tissues or foreign bodies without subsequent excision or retrieval, if desired. Embodiments may also comprise structures and functionality for the different phases of the surgical procedure, which may comprise stopping, repositioning and re-starting the procedure in a minimally invasive fashion. Embodiments may be used in single insertion-single retrieval, single insertion-single isolation, or single insertion-multiple isolation modes. Embodiments may be configured to be portable, disposable, recyclable or reusable and may be electrically, mechanically and/or manually powered and operated.

Embodiments may also comprise or enable:
  the capability for pre-procedure treatment of an area and/or of a tissue or foreign body;
  the delivery of tracer materials for tracking the potential spread or flow patterns whereby tissues (such as cancerous tissues) may metastasize;
  the pre-procedure or intra-procedure delivery of medications that may anesthetize tissues on the way to at the site or upon leaving the site, or other therapeutic agents such as pro-coagulants and others;
  the delivery of intra-procedure or post-procedure materials, including but not limited to medications, implantable materials for cosmetic or therapeutic purposes (including but not limited to brachytherapy sources or transplant tissue or cells), and other implantable elements such as marking devices for later imaging reference; and
  the provision of a direct path to the site for a removable fiber optic cable to deliver light energy or enable visual inspection of the site.

Embodiments may also comprise capabilities for other techniques such as over the wire (Needle Loc) or percutaneous locating tube entry methods to approach a target tissue or foreign body. Embodiments may also comprise the use of vacuum-assisted collection and retrieval methods to among other purposes, aid in the control of movement of tissues (including but not limited to cells and fluids) and other materials from the target site to a site external to the body, or to provide such materials for analysis or any other procedures, including transplant. Embodiments may also comprise the use of radiofrequency (RF) energy powered cutting elements and structures. Embodiments, along with associated related subcomponents described herein, may be configured to provide the capabilities, in automatic or semi-automatic modes, to capture, immobilize, isolate, excise and retrieve solid, contiguous and/or fragmented tissues, foreign bodies and other materials as well as liquid and semi-solid tissues as well as the delivery of gasses, liquids, semi-liquids or solids to the site post-procedure. Such may be carried out for, among other reasons: histopathology, polymerase chain reaction, or any other analytical procedures; diagnosis; treatment; transplant; cosmetic procedures; or any other desired procedures.

BRIEF DESCRIPTION OF THE DRAWINGS

FIG. 2a is a top down view of a tip's path and FIG. 2b is a side view of a same tip path as it leaves a mouth of a tube chamber;

FIG. 3a is a top down view of a path of a tip of a curved tip, according to one embodiment. FIG. 3b is a side view of a path of a tip of a curved tip, according to one embodiment. FIG. 3c is a side view of a curved tip of a rod element as it would be in its final shape and position relative to a theoretical sphere it circumscribes after having completed its penetration/rotational travel from a mouth of a tube chamber, according to one embodiment. FIG. 3D shows representative spiraling grooves.

FIG. 4a, FIG. 4b, FIG. 4c. FIG. 44d FIG. 4e and FIG. 4f are side views of a number of rod element curved tip shapes according to embodiments, including different sizes, different appendages that are configured to expand laterally as a tip element curves into its natural shape upon leaving a tube chamber, and different cutting edge variations, according to embodiments. Also illustrated in FIG. 4g, FIG. 4h. FIG. 4i and FIG. j are cross-section of various shapes of a curved tip element 5, according to embodiments. Lastly, FIG. 4k, FIG. 4l and FIG. 4m show a locating wire (typically abbreviated "Needle Loc") for optional use with a device, according to embodiments.

DETAILED DESCRIPTION

Figure 1:
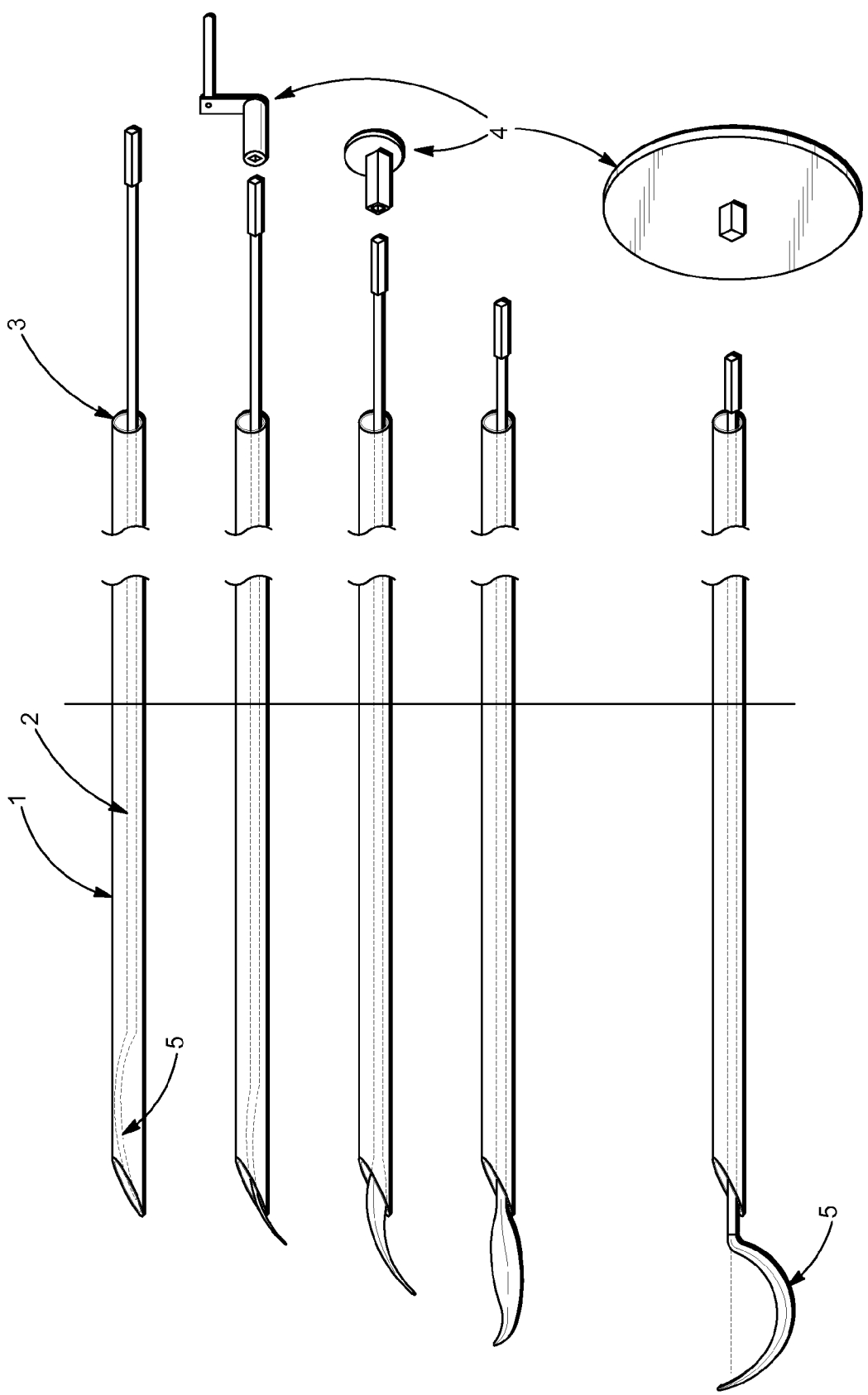
FIG. 1 shows a device according to one embodiment, and shows different phases of deployment thereof.

Reference will now be made in detail to the construction and operation of embodiments illustrated in the accompanying drawings. The following description is only exemplary of the embodiments described and shown herein.

Biopsy and other surgical procedures are used to remove tissues for histopathology analysis or for therapeutic reasons in many areas of the body. Techniques for these procedures have evolved over time, from simple open surgical biopsy as a traditional procedure to the use of advanced biopsy devices that are designed to provide a less invasive or minimally invasive alternative to traditional open surgical biopsy. The challenges for all such procedures and devices are to be able to approach a target tissue that is a candidate for biopsy or complete excision with minimal disturbance to sensitive surrounding tissue on the way to or in proximity to a target tissue; to effectively surround a target tissue without disturbing it in order to capture, immobilize (where this is necessary), isolate and excise a target tissue; to ensure clear margins of healthy tissue around a target tissue in the event that the procedure is a lumpectomy and to provide for effective post-procedure follow-on treatment of the cavity as determined necessary. Embodiments are designed to meet all of these challenges, including capabilities to isolate a target tissue or foreign body and, where desired, a clear margin of healthy tissue from the surrounding area while avoiding sensitive tissues and body structures on the way to and in the vicinity of a target, thereby minimizing damage such as severing, puncturing through, contaminating, etc., to surrounding structures, such as blood vessels, nerves, lymph nodes, adjacent organs, chest wall, and others; and then to remove a target from the body for analysis or any other procedures, and subsequent therapeutic treatment of the resulting cavity; accomplishing all of this with minimal invasion/tissue damage during the entire process, not simply on entry into the body.

Embodiments enable a complete removal of target tissues or foreign bodies in a single percutaneous entry pass, while at the same time leaving behind an optimized spherical or other three dimensionally shaped cavity for further treatment methods, some of which are extremely dependent for their effectiveness, reaction timing and avoidance of collateral damage to nearby tissues on as spherical a cavity as is possible to achieve. Such post-procedure treatment (radiation therapy, drug eluting implant therapy, and others where it is desired to uniformly treat the tissue on the walls of the cavity but not beyond it, or with too much treatment adjacent to one cavity wall while not effectively or efficiently reaching the other side of the cavity) has been shown to be most effective under such conditions. Embodiments may be configured to enable effective core sampling for analysis biopsy procedures as a follow-on procedure (where a targeted tissue site is known or suspected to be carcinogenic, for instance) to completely remove a target tissue with clean margins of healthy tissue as soon as practicable, using the same entryway created by core sampling biopsy devices, and to leave behind an optimized spherical or nearly spherical or other optimally shaped cavity from whence the suspect tissue was taken. In addition or alternatively, the embodiments may be used as a preventive measure, either through complete removal of a target tissue or foreign body using these embodiments or by alternate means, such as manual surgical removal of the target tissue following tissue isolation using these embodiments or through simple isolation of a target tissue or foreign body for subsequent clearance by the body's immune system or injected substances.

Use of embodiments to isolate a tissue or foreign body without subsequent removal from the body (at least immediately) may accomplish several important surgical and therapeutic goals, including cutting off the blood supply to a tissue, preventing invasion of a tissue into surrounding tissues, or simply allowing the body's immune system a chance to attack and clear a tissue or foreign body from all sides once the target has been weakened by isolation. When one or more of these objectives has been accomplished, a target may begin to diminish in size and/or viability over time, providing the opportunity to periodically re-evaluate the target with various imaging and other diagnostic techniques (such as ultrasound, CAT-scan, PET-scan) and allowing the physician to design follow-up treatment(s) (radiation, chemotherapy, subsequent open surgical excision, and/or any other treatment options applicable) at the most optimum rate and schedule and as the patient is able to tolerate treatment. Embodiments have the advantage of enabling a choice to decrease the dose or change the type of the treatment(s) required, particularly if the target diminishes over time, in order to minimize toxicity and other undesirable side effects of such treatment(s). Simple isolation of a target with minimally invasive procedures as enabled by embodiments and without (at least immediate) subsequent removal from the body may in fact be necessary in some cases. Such cases may include, for example, situations when a patient is significantly compromised and/or in a decompensated state and not able to tolerate the target removal procedure; when a target is in a very sensitive area that may not allow for withdrawal of the target through a percutaneous approach site; when the target contains toxic material, for example, an encapsulated abscess; when the target is friable and therefore not a desirable candidate for removal (at least immediately after isolation); or any other situation where removal of the target (at least immediately after isolation) is not advisable or possible.

FIG. 1 shows several illustrations of a device 1 according to one embodiment. As shown, the device 1 may comprise a rod element 2 comprising a curved tip portion, loaded inside a non or differentially rotating tube chamber 3, and actuated by a rod actuator 4 (including, but not limited to, being disk shaped or simple crank, cam, or other gear system). The rod actuator 4 may be configured to engage the proximal end of a rod element 2. The vertical line passing through all five of the illustrations of the device 1 represents an exemplary percutaneous entry point into the body to show relative positioning of the elements of the device in use. The illustrations, from top to bottom, show various phases or positions, including:
(a) at-rest (loaded) position;
(b) initial penetration/start of rotation/start of a curved tip 5 extension position;
(c) continued penetration/continued rotation position;
(d) half-way penetration/half-way (approximately 90 degrees of rod rotation from rest position within the tube chamber) rotation position, and
(e) fully deployed (approximately 180 degrees from rest position), which denotes the end of both forward penetration (axial extension from) and rotation of a rod element 2 within a tube chamber 3, as well as showing that a curved tip 5 of a rod element 2 has achieved its natural shape, as opposed to its relatively flattened shape within the tube, as seen in the top illustration.

Such action may also be accompanied (not illustrated) by rotation of a tube chamber 3 during forward penetration/rotation movement of a rod element 2. FIG. 1 shows the relative positioning of a rod element 2 with a non- or differentially rotating tube chamber 3 at various phases of deployment. The curved tips of a rod element 2 may be configured to be flexible, and may be flat or nearly flat when initially loaded into a tube chamber 3 (position (a)), to thereafter gradually assume their natural fully-deployed shape (half circle or other desired shape), as shown in position (e), having rotated on a rod element axis approximately 180 degrees, in this instance, from their initial position in a tube chamber 3. To enable such tip action to occur, the rod element may be constructed of springy material, such as metal alloy, carbon fiber, or a shape-memory material such as, for example. Nitinol®, a Nickel-Titanium alloy. It is this combination of axial movement, coupled with rotation of a rod element with its curved tip, and coupled with spatial revolution of the tip and sides of a curved tip along with other motions that enables the functionality of the embodiment.

The rod element 2 may be loaded into a tube chamber 3 with a curved tip 5 flattened inside the tube chamber to enable the device to have as small an initial tip cross-section as possible which, in turn, allows for percutaneous insertion into the body (minimally invasive) and continued minimal invasion as the tip of the device 1 advances toward a target tissue or foreign body site, either following the path of a previous device and procedure, or in making its own path to a target site. Only when in proximity to a target site is it desirable to deploy the curved tip 5 from the tube chamber 3 around a target tissue without penetrating such target tissue, and even then, the path of a tip of curved tip 5 may describe a minimally invasive pattern, which may result in final positioning of a curved tip before rotation to carve out a spherical or near spherical shape to isolate a target tissue, lesion or foreign body from surrounding healthy tissue without disturbing such a target. In this manner, a sphere or near spherical shape may be isolated, which shape is, by definition, the least invasive three-dimensional shape that can contain a target tissue of a given size and diameter, unless a target is unusually and atypically shaped. For instance, if the target tissue is very long compared to its diameter, a different curved tip shape may be selected to accommodate such a target tissue. The tube chamber 3 may also serve as a delivery tube for medications and other materials. The tube chamber 3 may also be connected at its proximal end (to the right on the drawing) to a vacuum apparatus for collection of fluids, cells and other materials from a target site for disposal, for later histopathology analysis or any other desired procedures.

According to one embodiment, rod element 2 may be hollow with apertures along the curved tip 5 to elute anesthetics, other medications, or other materials intra-procedure, and may be coupled to a radiofrequency (RF) energy source at its proximal end, if desired, to enhance its tip penetration/side cutting efficiency. In that case, the tube chamber 3 may be provided with an inner surface treatment having insulating characteristics, or alternatively, the tube chamber 3 may comprise a non-conductive and RF energy resistant material. The base end of the shaft of the rod element 2 may be configured to positively engage and lock into rod actuator 4, specifically for the purpose of controlling, with the tube chamber, the rod's penetration and withdrawal from a target site and the body.

Figure 2B:
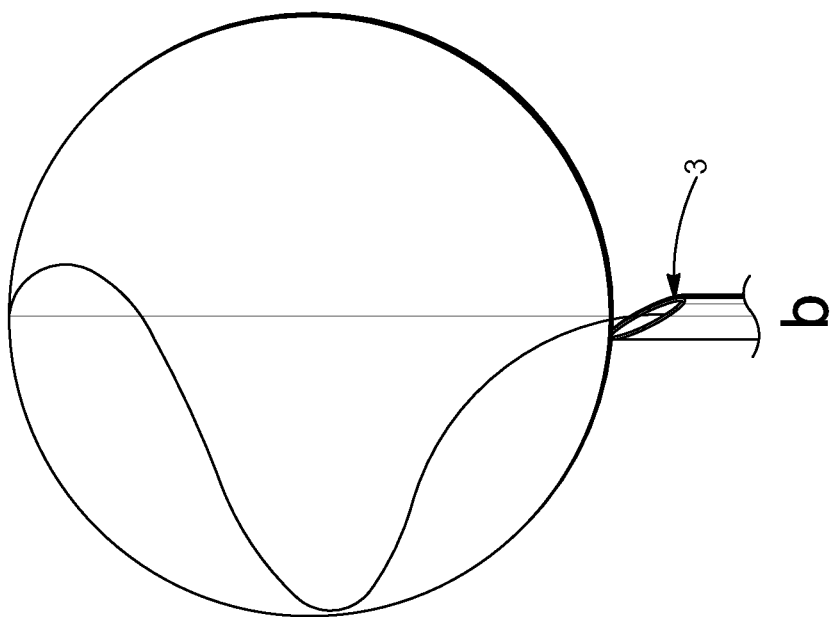
FIG. 2A and FIG. 2B shows two perspectives of the spatial travel of a tip of a rod element deployed from a tube chamber, according to one embodiment.
Figure 2A:
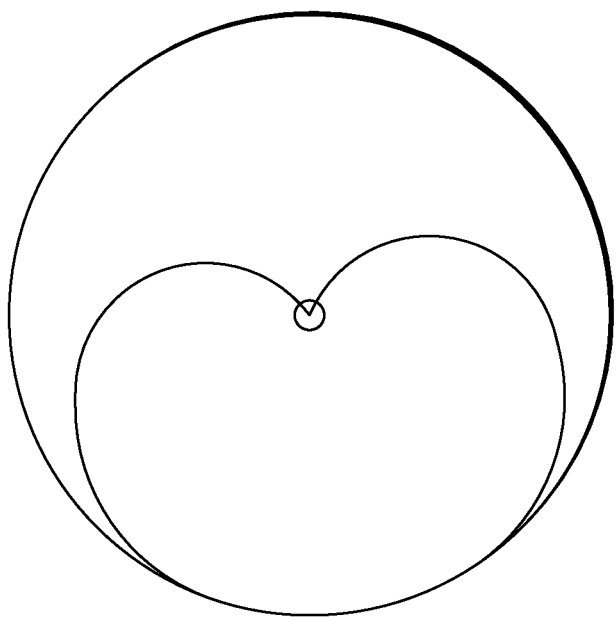
Figure 3C:
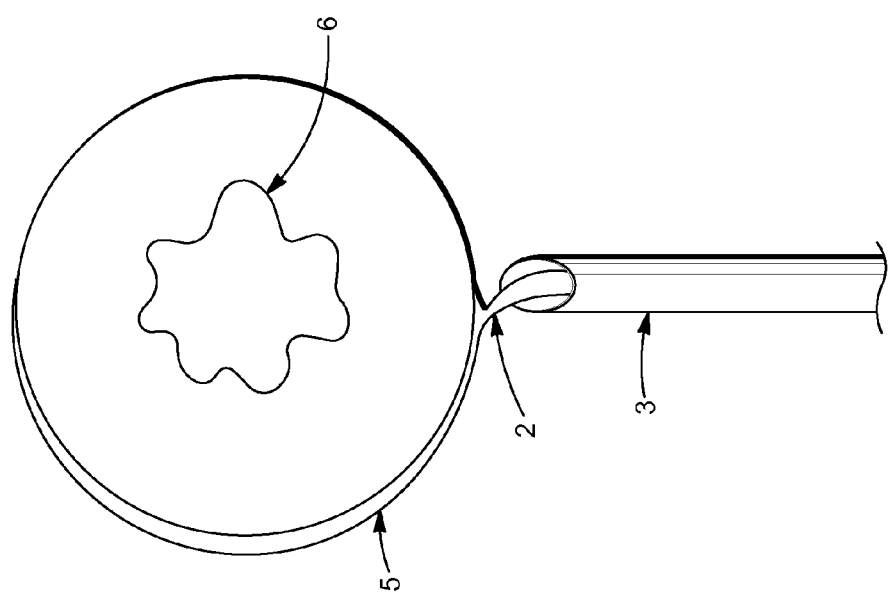
FIG. 3A, FIG. 3B, FIG. 3C and FIG. 3D illustrate several embodiments of a sphere or near spherical shape that may be configured to be circumscribed by a tip of a single rod element, following a path shown in FIG. 1 and FIG. 2A and FIG. 2B, and assuming that a tube chamber is also rotated at the same time.
Figure 3D:
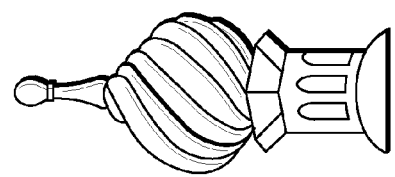
Figure 3A:
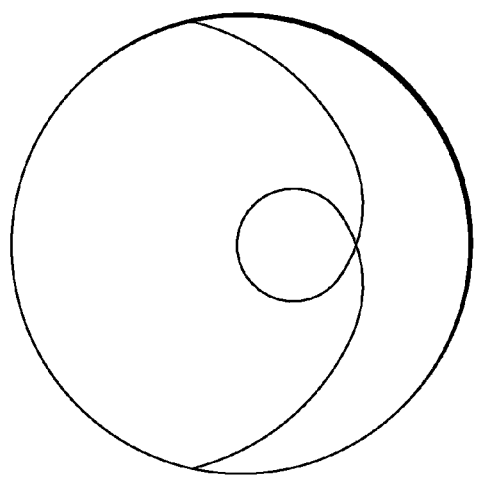
Figure 3B:
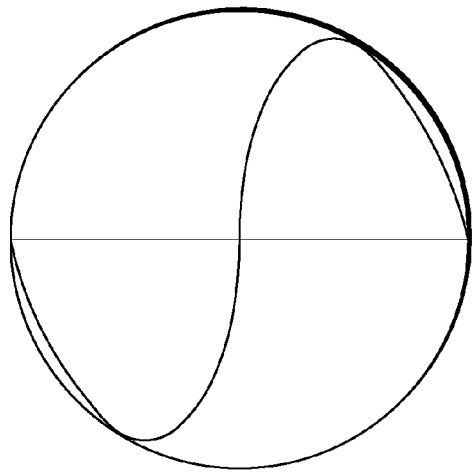

FIGS. 2A and 2B show two perspectives of the spatial travel of the tip of a rod element 2, according to one embodiment. FIG. 2A is an end on (polar view) illustration of the three-dimensional path taken in space by the very tip of the curved tip of rod element 2 as it penetrates forward (up out of the plane of the illustration) while rotating optimally approximately 180 degrees from its initial rest position within tube chamber 3. This illustrates that the overall shape of, and assumed by, the curved tip as it is released from its chamber tube. The relative speed of rotation and the speed of penetration, if precisely coordinated, act in concert to cause the tip to describe a three-dimensional path, similar to that of drawing a spiral line on the outside of a sphere, and that a tip, after having rotated at least 180 degrees from its initial pointing position, will arrive at the top pole of the sphere without having disturbed any point within the sphere. One embodiment comprises circumscribing an additional path in space of the sides and tip of a curved tip 5 of rod element 2 if the tube chamber 3 is also rotated synchronously with the rotation/penetration movement of rod element 2. FIG. 2B is a side view of the same tip path as it leaves the mouth of a tube chamber 3, (which may be non- or differentially rotating), penetrates up and around a theoretical spherical shape in space, from its initial position at the bottom (proximal pole of the sphere) to its final position (top or distal end of the sphere shape), according to one embodiment. The circumference of the sphere itself describes the path the side of the curved tip 5 would carve spherically when rotation continues following full tip deployment.

FIG. 3 show several illustrations of the action of a curved tip 5 under combined axial/rotational/revolution movement, according to one embodiment. FIG. 3A is a top down view of the path of the tip of a curved tip 5, according to one embodiment. FIG. 3B is a side view of the path of the tip of a curved tip 5, according to one embodiment, assuming that a tube chamber 3 is simultaneously rotated with rotation of a rod element 2 within it, as rod element 2 travels axially forward (up in a side view). FIG. 3C is a side view of curved tip 5 of a rod element 2, according to one embodiment, as it would be in its final shape and position relative to the theoretical spheroid or surface of revolution it may have circumscribed after have completed its penetration/rotational/revolution travel from the mouth of tube chamber 3. If, having reached this position, rod element 2, with or without simultaneous rotation of a tube chamber 3, was rotated about its own or common axis, the sharpened edges of a curved tip 5 may carve out a sphere-like shape, isolating it as a ball or sphere from the surrounding tissue and containing a targeted tissue or foreign body 6 in its center. Many factors may influence the perfection of the spherical shape that can theoretically be carved by the complex motion combination of axial penetration, rotation and complex (multiple) revolution, including a curved tip shape, resistance to bending or flexing, relative speeds of the motions involved, tissue density and uniformity of matrix, etc. The resulting three-dimensional shape carved out, according to one embodiment, may resemble that of a typical onion dome found architecturally on Eastern European monuments as sketched in FIG. 3D. The spiraling grooves that are shown in FIG. 3D may be considered representative of the paths taken by curved tips 5 of multiple rod elements 2. If desired, once a target tissue or foreign body has been removed, a second pass with the same instrument in a configuration in which the tips thereof are fully deployed may be carried out, rotating within the cavity to shave off additional tissue from the walls of the cavity remaining after the target tissue or foreign body has been removed. According to other embodiments, a different tip may be substituted, with vacuum, to shave the outer walls of the cavity and retrieve tissues including, for example, cells and fluids, foreign bodies, and other materials down a central tube.

It is well-documented that the fewer disturbances there are to the surrounding tissue in the area of a target tissue during an excision procedure, the better the recovery from the procedure with respect to post-procedure effects such as bleeding, nerve damage, and other adjacent structural damage. Also improved are speed of healing; overall patient well-being in terms of post-procedure pain, immune system response, potential inflammation and other complications; and in some cases, the cosmetic result. Advantageously, embodiments enable a the unique action and spatial orientation of deployment of the distal end of the device to surround a target tissue, or foreign body surrounded by soft tissue, to capture, immobilize, isolate from all surrounding healthy soft tissue structures, and withdraw it from the body, may all be conducted in a minimally-invasive manner, with little or no damage to surrounding body structures. Indeed, embodiments feature axial movement of the tips of individual rod penetration elements from tube chamber(s), with simple rotation and forward (axial) movement coupled with complex revolution of those same elements.

According to one embodiment, the rod elements may be configured to rotate upon their own axes, and circumscribe a predetermined path while the device itself revolves. According to one embodiment, the rod elements may also be configured to travel axially as well, giving them their own spiral orbit path until they are fully deployed at the North Pole of the spheroid collectively circumscribed by the advancing and rotating rod elements. Significantly, according to one embodiment, there is no violation of the center of the target tissue within the tissue spheroid that the rod and tip elements circumscribe, as the device does not penetrate the target tissue. This is made possible because the rod and tip elements, as they emerge from the base axis of the device, may be configured to complete their course of movement without the need for a central supporting pole or being joined at their tips. Indeed, embodiments enable the excision and isolation of target tissue without the need for any central penetrating structure, as described in detail below. Advantageously, pathologic analysis of the isolated/retrieved tissue specimen is not hindered by any alteration of the tissue itself within the spheroid. According to one embodiment, the device thus keeps the tissue specimen as close to its in-situ form and architecture as possible.

In one embodiment, a thin guiding wire may be used as a guiding element to the target. Such guiding wires, however, are slight in cross-section and may be left within the retrieved specimen when it is delivered for histopathological examination. The guiding wire within the target may also function as a reference landmark. One embodiment, therefore, may be configured to combine, coordinate, and incorporate axial motion, simple rotation and complex revolution movements of its various components in order to deploy, from a minimal initial tip cross-section, a structure that may be configured to surround, capture, immobilize, isolate, excise and/or retrieve a target tissue, or foreign body surrounded by normal tissue. Embodiments also may be configured to collect other materials from a target site and deliver still other materials to a target site.

FIGS. 4a through 4m show several embodiments of the curved tip 5, showing different shapes, cross-sections, and locating wire shapes (referred to as a "Needle Loc" and used to mark a location of a suspect tissue within the body pre- or intra-procedurally). FIG. 4a shows several standard dimensions (not to scale) that may be envisioned for the curved tips 5 for use with different size target tissues to be isolated or excised, as well as for subsequent cavity shaping, according to embodiments. One embodiment of such curved tips may comprise a tip extremity extending over center and may also comprise a proximal spur where a curved tip 5 extends from a rod element 2, all of which may aid complete part-off of a tissue that may be surrounding tissue or a foreign body to be isolated or excised with at least one full rotation of a rod element 2 or revolution of a rod element 2 within a tube chamber 3. The tip extremities extending over center may serve to lock with other curved tips at the end of their full deployment. FIG. 4b shows another embodiment of a curved tip 5 comprising barbs that may be configured to deploy laterally upon release from a tube chamber 3, according to one embodiment. Such barbs may serve multiple purposes, including stabilizing a tissue or foreign body after it is carved out in three dimensions, increasing the surface area of a curved tip 5 for a better grip on a target to be isolated with excision, and maintaining that grip on a tissue to be excised when withdrawing it through a relatively narrow entry pathway.

FIG. 4c illustrates another embodiment comprising a curved tip 5 that is not only curved, but partially spiraled in form as its natural shape. Such a shape may describe a more perfect theoretical sphere from some types of tissue. Additionally, this illustration shows an embodiment of a tip configuration that is bent up at its extremity, which may enable it to ride over the surface of the sphere to be carved out, as opposed to digging into the sphere. FIG. 4d illustrates yet another curved tip 5 embodiment where a curved tip may comprise one or more elements that are joined at the distal and proximal ends, or may be leaf-shaped. This may increase the surface area of a curved tip 5 in relation to the spheroid surface of a tissue or foreign body to be isolated or excised. FIG. 4e shows a curved tip 5 in non-spherical natural state, according to one embodiment, which may result in a different three dimensional form (other than a spherical shape) if such is the goal, as where a spherical shape might too closely approach an adjoining body structure, such as an organ or chest wall, and it is still desired to extract an efficiently shaped target specimen, leaving behind a reasonably shaped cavity for post-operative therapeutic measures or where a target tissue has an elongated shape, for example. FIG. 4f shows one possible treatment for sharpened edges of a curved tip 5 which, according to one embodiment, may be serrated as shown with tip interlocking characteristics upon full deployment, with eluting holes between serrations (not shown), or any other effective configuration, including relatively blunt edges if radiofrequency (RF) energy is to be used as a cutting mechanism enhancement for a curved tip as it rotates for tissue separation.

FIGS. 4g through 4j illustrate various possible cross-sections for a curved tip 5 according to embodiments, which may vary from one to another along the chord of a curved tip 5. FIG. 4j shows a so-called tanto point, which is effective in penetrating, distally and parting dense tissue and materials laterally. This point also has the advantage of being single edged, which is one possible cross-section configuration, This point also has the advantage that with a leading sharp edge, such as suggested at reference 67, for forward penetration/rotation, it also has a blunt opposite edge, which may limit tissue damage if curved tips were to be withdrawn back along their retraction/rotation pathway. Lastly, this particular cross-section 4j may be used with or without RF energy very efficiently, since it would have both a sharp edge for non-RF use and a relatively blunt edge, which may function to diffuse the RF energy along the edge for forward cutting from such a surface. Any of the cross-section shapes may also aid, with a slightly raised spine (FIG. 4g) in aiding tissue penetration under rotation, increasing stiffness of a curved tip 5 in desired areas along the curve, or other purposes. Finally, Figs, 4k, 4l and 4m illustrate three embodiments of locating wires and tips, which n ay be used as one component of this device. FIG. 4k shows such a locating wire 8 with a fixed pointed cap, which may be useful in assisting, a curved, tip part-off at one phase of the procedure. FIG. 4l shows such a locating wire 8 with a hinged barb tip, which may be used to penetrate a target tissue or foreign body completely, and then to be withdrawn at the end of the procedure with the rest of the device and target sample for direct correlation between what was originally imaged for targeting and what was actually excised, while also aiding in maintaining the specimen in the cage of the extended curved tips during withdrawal. In this case, for example, the pathologist may request that at the end of the procedure, the entire device be placed into a sterile container for delivery to the pathology lab, where it may be digitally photographed to record the direct correlation before the target excised is released from the device and analyzed. These locating wires, according to embodiments, may also be used to immobilize a target during the procedure, especially if the target has a tendency to try to displace itself during the operation, and to aid in keeping a target in contact with curved tips 5 during withdrawal. FIG. 4m shows yet another new type of locating wire and tip, according to another embodiment. This tip, which may be very precisely matched to the inside diameter of a central tube 7 of FIG. 5 and other figures, may be used as a ramrod to deliver materials, such as markers, directly to a target site, may also assist in the delivery of other liquids and semi-liquids, such as anesthetics or other medications or transplantable materials, and finally may also be used as a very simple vacuum device, to replace or augment another vacuum system to draw materials, including but not limited to liquids and cells, from the site before withdrawal of the device from the body.

These materials may then be emptied into a sterile container to enable later histopathology or any other type of analysis post-procedure, or simply delivered (to a pathologist, for example) with the rest of the device in a sterile container, as appropriate. Other uses of the locating wire shown in FIG. 4m, according to embodiments include to gently release the tissue or foreign body obtained from the tip of the device upon complete retraction of curved tips 5 of the device (similar to a ramrod inserted into a central tube 7 from the proximal end), for release of a material delivered to the site by the device, for use intra-operatively to clear a central tube 7 of any blockage, for use in assisting parting-off, if necessary, of the proximal end of a tissue or foreign body to be isolated or excised if the edges of a flat plate tip are sharpened as well, and even as a localized energy (such as RF) diffusion source. Special locating wires that may be supplied with the device may be graduated along their length, which may enable the operator to directly read the distance from the distal end of a central tube of known length to a target, if the tip of a locating wire was placed into or in known and measured proximity to a target, as verified by image guidance or other techniques. According to one embodiment, the locating wire may also not be an actual wire at all, but a fiber optic cable or electron beam apparatus, with a diffusing tip, or a tube which may be shaped as necessary—round pointed, flat disc, inverted funnel, mirror-ended or any other shape. Other shapes, configurations and apparatus are possible.

Figure 5:
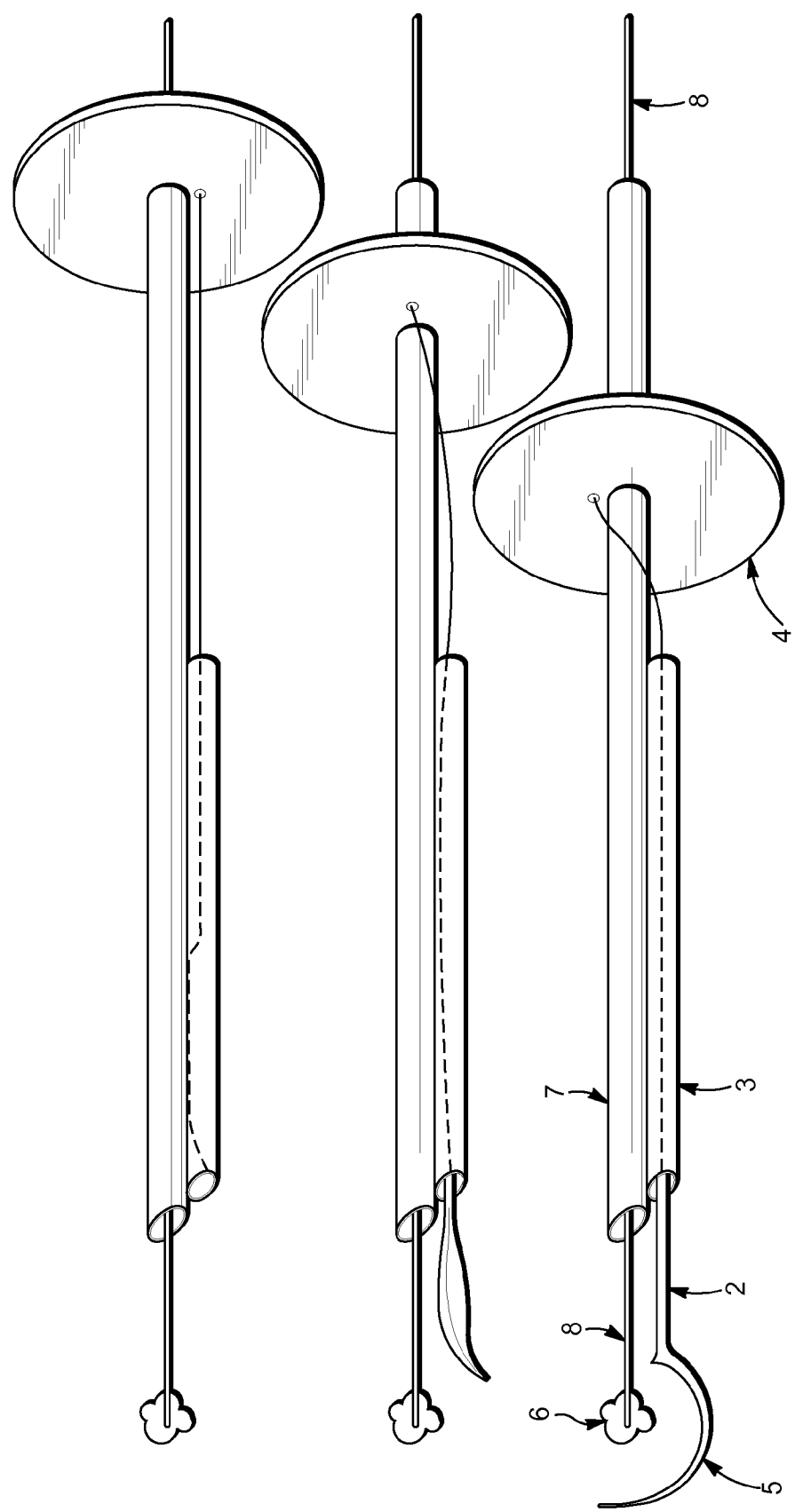
FIG. 5 shows three views of a continuum of motion, from top to bottom, in the deployment of a rod element from a tube chamber, according to one embodiment.

FIG. 5 shows several side views of the device 1, according to one embodiment. As shown, a non- or differentially rotating central tube 7 (not necessarily to scale) may be coupled to a tube chamber 3 with its rod element 2 in various phases of deployment. In this illustration, an actuating disk 4, similar in function to that shown in FIG. 1 above, may be centered on central tube 7, and to which may be attached the proximal base of rod element 2. Axial movement of such an actuating disk 4, independently of any rotation of central tube 7, coupled with rotation of such a disk around central tube 7 results in a twisting motion on rod element 2 which, in turn, orients curved tip 5 approximately 180 degrees from its original pointing position at rest within tube chamber 3 by the end of its travel. Such a central tube 7 may also be capable of sliding axially with relation to tube chamber 3, and may be located in its own central sleeve. The tip of central tube 7 may thus be advanced axially toward a target independently of tube chamber 3 and either in conjunction with curved tip 5 of rod element 2 or independently of its motion.

The actuating disk 4 may be suitably configured to accomplish its stated purpose. For instance, instead of using a twisting motion on rod element 2 around central tube 7 to impart a curved, optimally 180 degree rotational movement to curved tip 5, according to one embodiment, actuating disk 4 may in fact be composed of a ring gear with a planetary gear driven by it and to which may be attached the proximal end of rod element 2 (the sun in this instance being represented by a central tube 7, which may also be surrounded by its own gear driving mechanism). The twisting movement of actuating disk 4 is significant, since it is both simple in conception, robust (few moving parts), easier to construct at very small scale, and has the advantage that once twisted, rod element 2 will tend to resist additional twisting, already being under torque tension in that state. This pre-loaded tension in torque, once achieved by the end of the lateral or axial travel of rod element 2, would tend to stiffen its curved tip 5, readying it for the next phase of revolutionary slicing with its edges to carve out the spheroid-shaped volume within the soft tissue. This pre-tensioning may tend to keep the edges of curved tip 5 in their plane and prevent them from twisting under side loads of cutting action, allowing them to always present their sharp edges or RF energy to the tissue path to be described, which would result in the least deviation from their intended path and avoid unnecessary collateral tissue damage in proximity to a target tissue or foreign body.

A significant goal is to accurately correlate tissue diagnosis with imaging diagnosis. In order to successfully accomplish this, it is crucial to know that the retrieved tissue actually and accurately represents the imaged abnormality. As illustrated, a central tube, with its other attachments in system, may be advanced laterally toward or away from a target tissue or foreign body over an optionally-used locating wire 8 (or to deliver a locating wire 8), which may have been placed into, near, or through a target 6 pre- or intra-procedurally, the latter case implying deployment of a locating wire 8 from central tube 7 upon arrival of the device in proximity to a target, for such uses as distance measuring to a target or for positive and accurate sighting of a target with or without image guidance.

The central tube 7 may also be used to move materials and other apparatus to and from a target site. Again, this figure illustrates the functionality of this device to allow placement of curved tip 5 in spatial relationship to a target tissue or foreign body 6, in preparation for revolution of the edges of curved tip 5 around such a target, without the curved tip 5 ever having disturbed the target 6 in its location within the surrounding tissue. The illustrations are not to scale.

Clinically and procedurally, the ability of a biopsy instrument to advance gently towards a target provides several advantages, not the least of which is avoidance of unnecessary tissue sectioning with the attendant damage to blood vessels, nerves and other organic structures. The ability of a biopsy instrument to advance gently towards a target also hastens recovery time for the patient, and reduces complications, due to the shorter length of the procedure (as compared, for example, to the length of open surgical biopsy procedures). A related benefit conferred by embodiments is to enable the device to not only advance gently towards a target, but also to gently and precisely deploy its working surfaces in proximity to the target.

Embodiments provide the operator with methods, mechanisms and functions to gently approach a target tissue or foreign body, deliberately deploy curved tips of penetrating rod elements around a target (the semi-automatic mode of the device being discussed below), and only then, if desired, and only then make the final decision to carve out the three dimensional spheroid shape of the surrounding soft tissue, within which the target tissue or one or more foreign bodies are immobilized and isolated, surrounded with clean margins of healthy tissue. This ability to position the device in relation to a target, still having minimally invaded the tissue that is penetrated, coupled with the ability to re-position if necessary in relation to the target, again with minimal disruption to surrounding tissue, and then the ability to complete the procedure when conditions are as perfect as possible gives inherent confidence in the device, its functionality, and in the approach to the procedure and the procedure itself on the part of the operator. Further, the device may be configured to function in single insertion, single retrieval, single insertion, single isolation or single insertion, multiple isolation modes, resulting in minimally invasive procedures across all such modes of operation.

Figure 6:
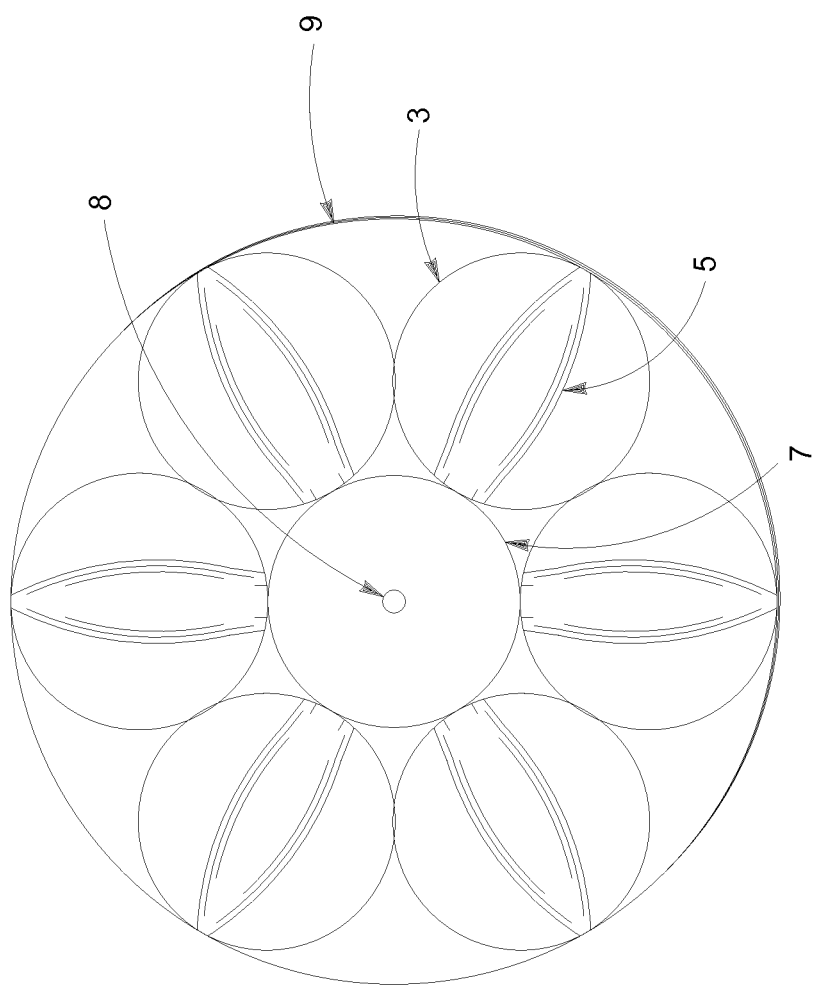
FIG. 6 is an end-on view of a distal end of an outer tube/penetration barrel, having placed within it a number of tube chambers, which themselves surround a central tube which may, in turn, be centered spatially within its own tube sleeve and/or over a locating wire, according to one embodiment.

FIG. 6 shows the distal end of the device 1 according to one embodiment, from an end-on perspective. FIG. 6 shows one embodiment of the device 1 comprising six tube chambers 3, each of which contains a rod element 2, arranged around a central tube 7, which may be configured to be free to move proximally or distally with relation to surrounding tube chambers, all of which may be enclosed in an outer tube/barrel 9. As also shown, central tube 7 may be advanced over a locating wire 8, or a locating wire 8 or other elements may be advanced through its core. The device, according to one embodiment, may comprise a central tube 7 running from its distal tip to its proximal extremity. In this manner, the proximal end of the central tube 7 may serve as a pathway through which fluids, cells, other materials, or contaminating materials may exit a percutaneous entry point of the device. Such structure enables control of fluids, cells and loose tissue (among other materials) from a target site and to capture and contain such materials for analysis (or other desired procedures), as well as to allow the delivery, intra-procedurally, of medications, anesthetizing agents, markers or other biologically-active materials or apparatus to a target site or resultant cavity via the device. In their pre-deployment or loaded position, the tips of curved tips 5 of rod elements may be oriented such that they point radially out from the center of the assembly.

Other configurations, such as embodiments in which the tips of rods are initially oriented inward are possible, with additional rotation and/or revolution then being necessary to bring the tips together over a target tissue or foreign body at the end of their paths. In this latter configuration, the tips of curved tips 5 may be machined (for instance, to a leaf shape) to completely close the ends of tube chambers 3 which are normally but not necessarily cut at an angle at their extremities like hypodermic needles. Finally, this embodiment builds on the embodiments shown and described relative to FIG. 5, but with the addition of a greater number of tube chambers 3 located around central tube 7, which may be located in its own sleeve. In fact, any number of such tube chambers may be placed around a central tube, in order to provide as complete coverage of the final basket shape (similar to the lines encircling a basketball) of the curved tips around a target as possible or desired, given the constraints of initial device tip cross-sectional limitations, physical characteristics of the elements of the device. Although a single tube chamber 3 may be contiguous to central tube 7, other embodiments provide for at least two tube chambers 3.

According to other embodiments, the device may not comprise a central tube 7, but may instead comprise a tube chamber 3 with a rod element 2. According to one embodiment, the tube chambers may be round in cross-section to avoid any conflict with rod elements and curved tips as they rotate, although they need not be round in cross-section. Other embodiments provide for pie-shaped or polygonal cross-section tube chambers, and such embodiments may serve to reduce the overall diameter of an outer tube. Additionally, the tube chambers may simply be bored through a single outer tube/barrel 9, which may also be made of an insulating material and additionally act as the sleeve of central tube 7. One embodiment does not comprise a central tube 7 at all, but only two or more tube chambers bored through a single outer tube/barrel 9, or contained within an outer tube/barrel 9. Contained within each tube chamber 3 may be a rod element 2 showing its curved tip 5 with the tips of those rod elements pointing radially outward from tube chamber 3 in their loaded, at-rest configuration. According to other embodiments, the tips may also be pointing towards the central tube 7 in loaded, at-rest configuration.

Figure 7:
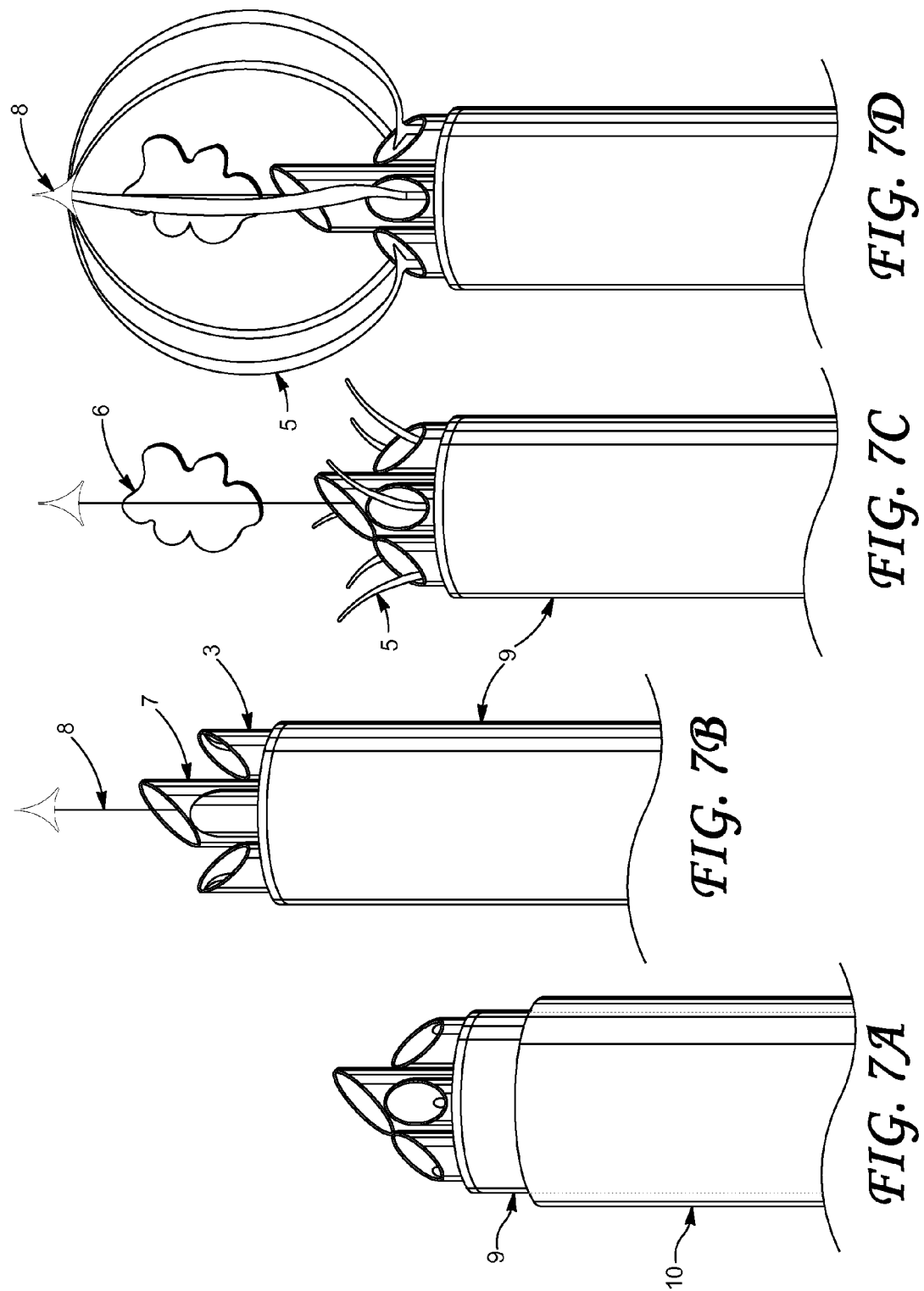
FIG. 7A, FIG. 7B, FIG. 7C and FIG. 7D show different side views of a distal end of one embodiment in various modes, according to one embodiment.

FIGS. 7A-7D illustrate different side views of the distal end of one embodiment in various modes of operation. FIG. 7A shows one entry configuration of an outer tube/barrel 9, in this instance with its own sharpened edge, rotating as a unit and approaching a target tissue or foreign body from inside of a previously placed locating tube 10, with the tips of tube chambers 3 oriented around a central tube 7 in a sharp, tissue penetration orientation. Since in this illustration it is advancing to a target site inside a locating tube that was pre-placed to provide a clear path to a target, an outer tube may not have to rotate at all to penetrate to a target site. FIG. 7B shows the distal end of an embodiment, penetrating tissue in rotation as a unit en route to a target site, this time over a locating wire 8, with the tips of tube chambers 3 optionally oriented around a central tube 7 and inside an outer tube 9 in a coring-type configuration for entering tissue in a pathway to a target that may not have been previously been utilized (i.e., not following a prior coring biopsy procedure's pathway to the target). The tips of tube chambers 3, if individual tubes within the outer tube, may be angled with relation to an outer tube 9 to present cutting teeth to facilitate coring penetration movement or such as to present a minimum tip cross-section with a sharpened tip cluster arrangement, such as the configuration of FIG. 7A. Alternatively, such a configuration may be molded or machined into the tip of such an outer tube/barrel with integral bored tube chambers. The tips of tube chambers and a central tube may also be configured to be flush with the leading edge of an outer tube/barrel in a different penetration mode. In the embodiments shown in both FIGS. 7A and 7B, curved tips 5 of rod elements are oriented radially outward from the tube chambers 3, although other orientations are possible, prior to beginning any distal penetration/rotation of their own once a target site is reached in proximity and straight ahead distally.

FIG. 7C illustrates the distal end of one embodiment, having arrived in position close to a target 6, and having advanced over locating wire 8, which in this instance has been placed through target 6, in the early stage of deploying curved tips 5 of rod elements 2. Here, it is assumed that an outer tube 9 may have already begun rotation in sympathy with that of rod elements 2 within tube chambers 3 in order to provide the axial penetration/simple rotation/complex revolution coordinated movement for each of a curved tip's optimal path. FIG. 7D shows the terminal phase of the action begun in FIG. 7C, with curved tips 5 in position around a target 6, and joined under the tip of a locating wire 8, in preparation for rotation of the entire distal end of the device as a locked unit, which would part-off and isolate a sphere-like shape of soft tissue enclosing a target 6, with such action being a distinct phase (semi-automatic mode of the device) or simple continuation of the action of the device distal tip (automatic mode of the device—from initial tip deployment to full deployment and rotation of the deployed curved tip basket for parting-off a target completely) from FIG. 7C. As also shown in FIG. 7D, a central tube 7, which may have graduation marks along its length, similar to graduations on the outer tube, has been advanced towards a target 6 during the procedure, an optional action that may, for instance, serve to assist immobilization of a target (for many reasons, including immobilizing or fixing a target as it is removed from the body) or to apply vacuum to the target to be parted-off, or for other reasons, such as distance measuring between the tip of a central tube 7 and the tip of a graduated locating wire 8, which can be read directly by the operator at the proximal end of the whole device, according to embodiments, or simply to establish the intended proximal boundary (a locating wire tip serving as the datum of the distal boundary, if used) of the clean margin of healthy tissue that is intended to enclose the target in the captured spheroid shape, according to one embodiments. This latter feature may also assist in positioning the distal end of the device in the absence of or in supplement to other image guidance systems used during the procedure, and in any case also may serve as a positive indication that an excised target tissue or foreign body corresponds to what was imaged and defined as the target, which is an indication of great assistance to a pathologist analyzing the captured and excised target and of great reassurance to the operator, post-operatively. Finally, a central tube may even be moved forward to penetrate a target for material or apparatus delivery directly to a target, or to further immobilize it, or for delivery of materials to a cavity left by excision of tissue post-procedurally, for example, if it is decided to withdraw the device and leave the central tube in place. Both a locating wire and a central tube may be pre-positioned, and a device according to an embodiment may be advanced to the target site over both of these elements.

Figure 8:
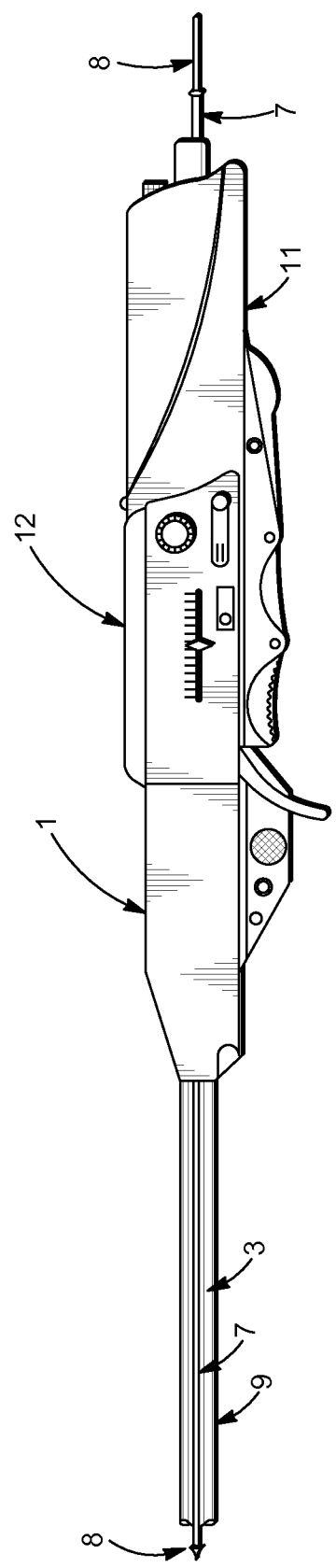
FIG. 8 is an external side view of one embodiment of the device of FIG. 1, illustrating various controls, indicators and features, according to one embodiment.

FIG. 8 shows an external view of one potential design for one embodiment of a device 1. The device, in such an embodiment, may be configured to comprise two major subsystems: a lower receiver/power/control unit 11 and a separate upper carriage/gear/tip unit 12, which may be changed intra-procedurally for another upper unit with different tip dimensions and/or configurations and, therefore, functionality, depending on the size of a target tissue or foreign body desired to be extracted, for subsequent cavity shaping and treatments, or other reasons such as therapeutic agent delivery or marker delivery, among others. This feature also adds inherent safety to the device. For example, if there is power or motor or control switch failure in the lower unit, the failed lower unit 11 may be swapped out for a replacement lower unit 11 during the operation, which can then continue to completion. The embodiment of the device 1 of FIG. 8 may comprise, as shown, an outer tube/barrel assembly 9, which encloses tube chambers 3 positioned around central tube 7, with the tip of a locating wire 8 optionally loaded into a tip inside central tube 7 and exiting from the proximal (rear) end of the device from central tube 7, which may extend all the way through the device. According to embodiments, controls may be disposed on the device for ambidextrous use, and provision may be made for attachment of the device to stereotactic tables for flexibility in ensuing operations. According to one embodiment, the upper proximal end of the device may be made of or comprise transparent material(s), thereby allowing for an operator to directly visualize the movement of the inner mechanism of the device (above the curved line towards the rear of the device).

Figure 9:
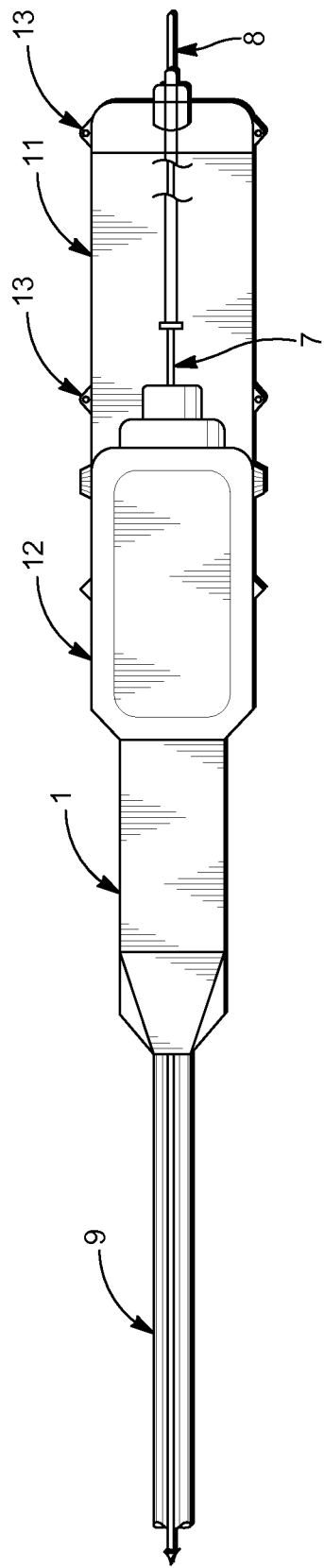
FIG. 9 is a top view of one embodiment of the device of FIG. 1, as shown in FIG. 8, according to one embodiment.

FIG. 9 shows a top view of the device illustrated in FIG. 8. According to one embodiment, the central tube 7 may extend through the device from distal tip to proximal exit point and may be the only element of the design to do so, assuming that an optional locating wire is not also loaded, thus serving to isolate a target at the target site, to prevent releasing fluids or materials from the site to minimize potential contamination, and to provide a vacuum-tight pathway and port through the device to a target site and resultant in-situ cavity. Also shown in this view are stereotactic table couplings 13.

Figure 10:
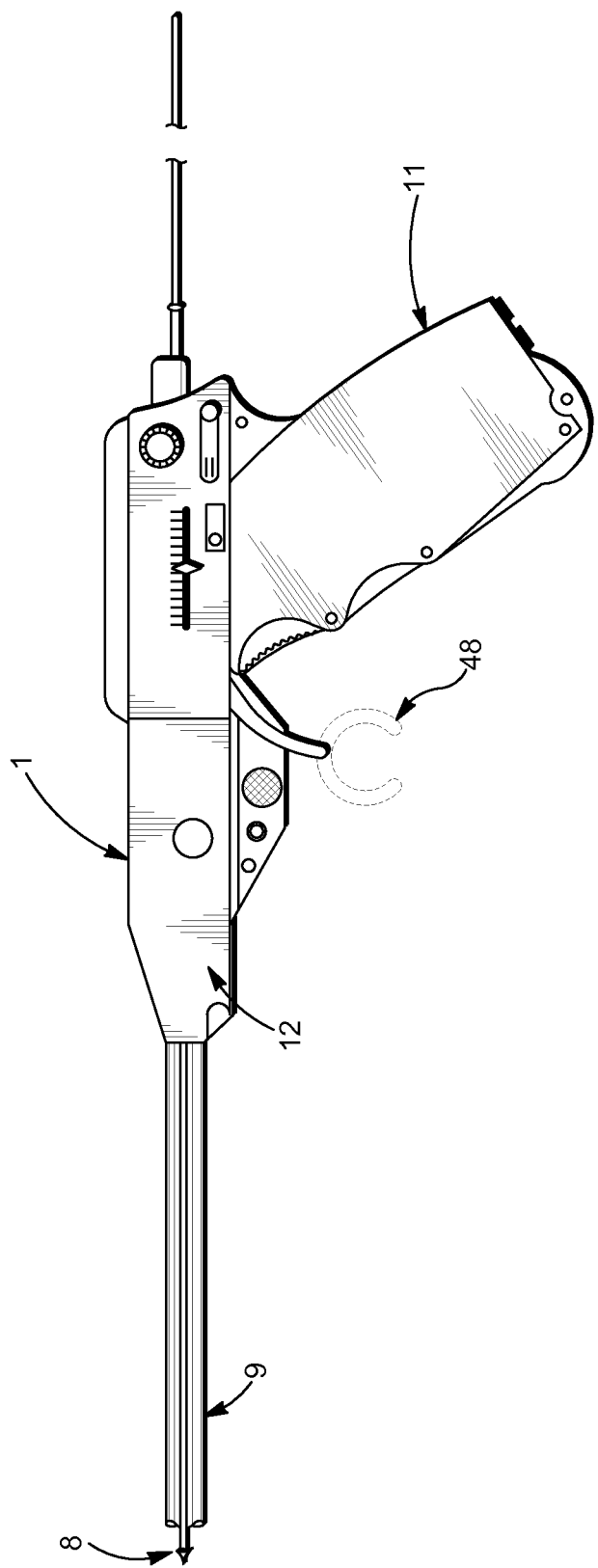
FIG. 10 is a side view of another configuration and embodiment of the device of FIG. 1, according to one embodiment.

FIG. 10 is an external side view of a variation of a design of device 1, according to one embodiment. The embodiment of FIG. 10 may comprise, as contrasted with the embodiment of FIG. 8, an arrangement for a lower power/control unit 11 under a replaceable/interchangeable upper unit 12, showing an outer tube/barrel assembly 9, an optional carriage slide lever extension 48, and a longitudinally displaceable central tube 7 of the barrel assembly with an optional locating wire 8 shown loaded into a central tube. The upper unit 12 may be manufactured by molding it of transparent material which would allow the operator to directly visualize the mechanical action of the carriage and transfer case, as discussed below. Such a feature may allow for an even greater level of comfort on the operator's part that the device is functioning as designed, since the tip of the device will not otherwise be visible, except under image guidance, during the operation procedure. Both the embodiment shown in FIG. 10 and the embodiment illustrated in FIG. 8 may be configured to function as hand-held, tether-less devices. Attachments such as RF energy connections, vacuum source connections, external power, liquid and solid delivery systems, fiber optic cable placement to a target site, etc. that may be connected to a multi-connection port 25 and an external power jack 26, shown in later figures, may provide add-on functional enhancement as optional attachments. According to embodiments, the device, by itself, will accomplish the essential operations of penetration, surrounding, capturing, immobilizing, isolating, and removing a target tissue or foreign body from the body, in its tether-less form.

Figure 11:
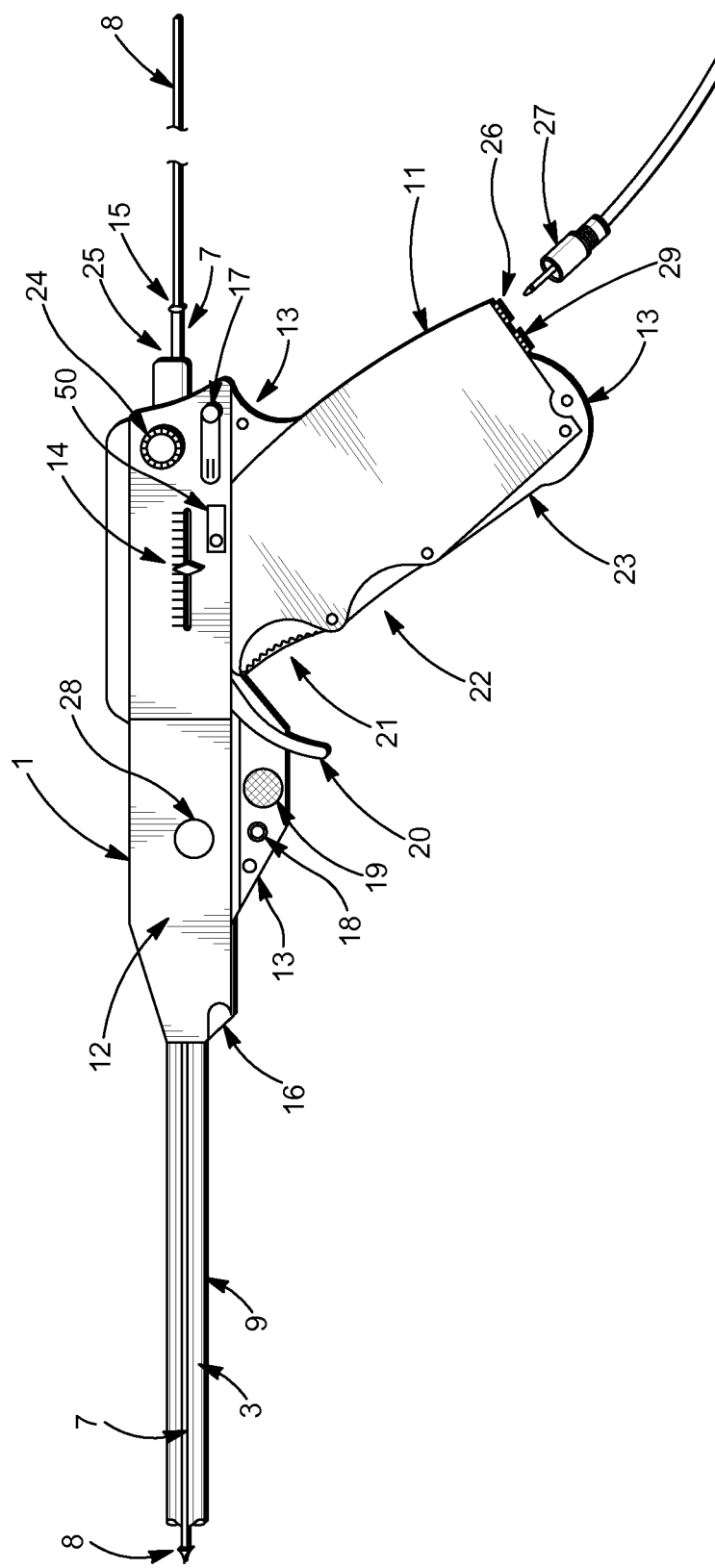
FIG. 11 is a side view of the device of FIG. 10, according to one embodiment.

FIG. 11 shows additional elements of the device of FIG. 10, according to one embodiment, and illustrates various element details and external layout of the ambidextrous operator controls and indicators. This embodiment provides for intuitive operations and controls. These structures are described in clockwise sequence around the drawing, starting at the distal tip end, as follows: A locating wire 8 running through the center of a center tube 7; a detachable and exchangeable upper mechanical/tip/carriage unit 12 of device 1; a gear lock button 28; a central tube axial movement indicator 14, which acts as an external depth penetration indicator and scale; an outer tube rotation-only selector switch 50; a central tube vernier knob 24 for advancement/retrograde action on the central tube for precise displacement distally or proximally of central tube 7 relative to outer tube/barrel assembly 9; a multi-connection port 25 (for locating wire/RF power/vacuum/fiber optic cable/delivery connections); a central tube/locating wire locking mechanism 15, which may also be placed after a separate port for vacuum running to a central tube (not shown); a locating wire 8; central tube 7; an upper unit locking lever 17; stereotactic table attachment or fixation points 13 (also located in two other places for stable three-point fixation in this design); a lower power/control unit 11; a lower unit external power supply jack 26; an external power cord 27; a battery cover lock 29; a tube assembly rotation switch 23; a curved tip retraction/rotation switch 22; a curved tip advance/rotation switch 21 having a series of grooves cut into its edge to allow the operator to distinguish it from a switch 22 by feel alone; an upper unit self-centering carriage slide lever 20; a forward/reverse tube assembly rotation selector switch 19; an RF power switch/indicator light 18; an upper unit hinge point tab 16; an outer tube/barrel 9; and tube chambers 3.

Main controls and indicators functions, according to embodiments and as described in FIG. 11 for the devices of FIGS. 8 and 10 may be as follows: a curved tip advance/rotation switch 21 functions to extend and advance, under rotation, curved tips 5 from outer tube/barrel assembly 9 once the tip of the device has been correctly placed in proximity to a target tissue or foreign body. Use of this switch also provides simultaneous, limited rotation of an outer tube/barrel in a ratio to the action of rod elements forward/rotational movement for optimum enclosure of a target upon the end of the movement (curved tips 5 meeting on the distal side of the target). At this point, the action may be stopped if desired, and the action is reversible at any time desired by withdrawing curved tips 5 into their respective tube chambers 3 using a rod tip retraction/rotation switch 22 if the operator is not satisfied with the device's initial placement. Additionally, the action of tip deployment from the distal end of the device may be controlled to happen very slowly and precisely, if desired, as a switch 21 configured such that first pressure will actuate a tip deployment/rotation/partial outer tube rotation at controlled speed (slow to fast with additional pressure) up to the first detent, which action will complete a tip deployment around a target but not part it off.

When such a tip deployment is completed, actuation of a micro-switch 60 (shown in FIG. 15) will stop further rotation of deployed curved tips. Taking pressure off such a switch at any time may serve two functions: to stop the action and to lock the device in its current position (for instance, tips partially deployed). Once past a first detent, with tips already fully deployed around a target, additional pressure—a second pressure—to a second detent will neutralize a micro-switch and cause an outer tube/barrel assembly to (or continue to) rotate, thus parting-off the spheroid of target tissue from the surrounding tissue. Such a switch 21, therefore, may be configured as a semi-automatic to automatic mode selector, since final rotational movement of the outer tube/barrel assembly for complete part-off of the target captured within the sphere created by the movement of curved tips will not yet have occurred if a first detent has not been passed (by definition semi-automatic mode). However, if the operator decides to press the switch past a first detent to a second detent at the very start of the procedure, the tips will fully deploy and the rotational parting-off of the target spheroid will follow automatically in this modality. The fully automatic modality may be used to great effect if the intent of the operator is to use the an embodiment of the present device as a single insertion-multiple isolation tool, and it is determined not to be necessary for the device to fully retrieve all of the isolated spheres of target tissues or foreign bodies thus created (the final one can be withdrawn at the end of the procedure if desired, of course), or when the operator is confident of having good placement of the tip of the device in relation to a target.

The fully automatic mode may thus be used for those procedures where time is of the essence in removing a target, or in procedures in which multiple targets are chosen for isolation with a single percutaneous entry of the device distal tip. It may be extremely useful to be able to rapidly isolate multiple targets, for instance with the use of RF energy (selected by, for example, an RF power switch/indicator light 18) to curved rod tips during the procedure, to completely part-off these targets from surrounding tissue, and at the same time cauterize the outsides of the spherical tissue specimens thus created while simultaneously cauterizing the inside of the cavities thus created surrounding the targets, which are simply left in situ, until further intervention. This isolation action may be all that is needed to treat certain targets, since this process cuts off and denies a blood supply to a target as well as controls bleeding at the site. The isolated target(s) may then be removed or left in place to be removed by the body's immune system. According to one embodiment the central tube 7 may also be extended into the target while it is still surrounded, immobilized and isolated by deployed curved tips of the device in the event that the target is intended to be left behind in the body and not removed, and would thus serve a purpose similar to a very precisely placed hypodermic needle to deliver an agent, such as an enzyme, virus, acid, marker dyes, lysing agents such as diazolidinyl urea or alcohol or other special drug or material, including removable radioactive sources or nano-particle drug or cell delivery materials as well as implanted materials that are targeted and delivered directly to a target to further assist or speed up the healing and/or clearance of the isolated, at present sealed target in its spherical shape, surrounded by clean margins, and if desired, a cauterized outer shell. The central tube 7, according to one embodiment, may also serve as a conduit for a fiber optic cable to be advanced to penetrate an isolated target for delivery of UV light, electron beam, LED light or diffused laser energy, similar to those techniques used in dermatology, or for an RF energy or heating and diffusing specially configured locating wire or other localized tissue treatment mechanism. This may be the final interventional phase, if desired, for a specific target, and once completed, tips of the device may be withdrawn into their respective tube chambers, the central tube retracted, whereupon the operator may then reposition the device to isolate another target while the device is still in the body. If desired, the operator can complete the procedure by removing the final target from the body.

If the operator continues to hold such an extension/rotation switch 21 in the fully on (at a second detent) position at the end of parting-off a target in either semiautomatic or automatic mode, the outer tube/barrel 9, along with the captured target in curved tips basket shape, may be configured to continue to rotate, allowing for easy withdrawal of the whole device tip from the body under rotation, using to advantage the principle of compound friction overcoming simple friction (i.e., it is easier to twist out a dowel from a tight hole than to try to just pull it straight out). According to one embodiment, the curved tip retraction/rotation switch 22, which may also be a rheostat for varying speed but with only a single detent, may be configured to withdraw the curved tips with the same degree of outer tube/barrel assembly 9 synchronized rotation as was used for tip penetration described above. This minimizes tissue damage proximal to a target site, since the tips of curved tips 5 follow a predictable penetration and retraction pathway, which is primarily characterized by a penetration rather than slicing motion, and any needed repositioning or re-aiming may be accomplished without excess damage to tissues surrounding a target site. The ratio of curved tip penetration or retraction under rotation to outer tube/barrel rotation may be dependent on different tissue matrices, and may be matched to the present device for each tip diameter that will be used (assuming for example that tips from FIG. 4a are standard tips for the device, which may thus be selected based on the size of the sphere to be created around different sized targets). Such a retraction/rotation switch 23 may be configured to have two other auxiliary functions. The first such auxiliary function may be to counter-rotate an outer tube/barrel assembly when entering the body from a percutaneous opening, for example, and in penetrating the whole tip of the device under this counter rotation towards a target site. A second auxiliary function of such a switch 23 may be to release an obtained tissue sphere from the curved tips of the device safely into a sterile container for transfer to the pathologist or other laboratory personnel, post-operatively, or to release a material to the target site, intra-operatively or post-operatively.

The outer tube/barrel assembly rotation switch 23, if comprised in such an embodiment, may, when engaged, cause simple higher speed/lower torque (than that of the action of switches 21 and 22) rotation of the outer tube/barrel in either direction, without affecting curved tip deployment, which may be used if desired for percutaneous tissue penetration to a target site (forward rotation, selected by a forward/reverse selector switch 19) with rod elements remaining in their individual tube chambers or for withdrawal of the device from the body upon completion of the desired phases of the whole procedure (reverse rotation, selected by a forward/reverse selector switch 19), or during a follow on procedure such as perfecting the cavity after removal of a target tissue or foreign body as preparation for subsequent procedures. This switch may be configured to be activated by an outer tube rotation-only selector switch 50. A gear lock switch 28 may be provided as a safety feature to positively lock the fully deployed curved tips in that position, regardless of rotation of any other element of the device. This may help ensure that a captured target would not be lost during withdrawal from the body. As is discussed hereunder, there may be no need to lock the gears when curved tips are not deployed and reverse rotation is selected by such a switch. An RF energy selector switch/indicator 18 may be used to turn on RF power current to switches 21 and 22, and also to indicate that the power is on using, for example, an LED light on a switch 18. According to one embodiment, the RF power may only be applied to curved tips for penetration/parting-off when either such a switch 21 or 22 is in use. A central tube vernier knob 24 and its position indicator 14 may be used by the operator to advance or retract a central tube axially within the device and in relation to a target, and to precisely note its position relative to other elements of the device (such as the very tip of the device).

A central tube/locating wire locking mechanism 15 may be used to lock those two elements together, which may be useful if, for instance, the tip of a locating wire is on the distal side of the target, and the tip of a central tube is on the proximal side of the target, with a distance between those two points equal to the distal and proximal poles of the sphere that will be carved out by the known fully deployed diameter of a curved tip basket. If so placed, the operator may be assured that a target will be fully captured in the ensuing phases of the operation. Finally, a carriage slide lever 20 operates a linkage 47 (shown in FIG. 14) that may be configured to move, axially forward or backward, the entire outer tube/barrel unit without affecting the placement of the device outside of the body. This feature's mechanical function is described hereunder relative to FIG. 15. Accordingly, if the entire outer tube/barrel assembly is moved axially during the deployment of curved tips by action of a switch 21, the resulting three dimensional shape of the tissue that will be captured and eventually parted-off will be modified from a spherical shape to either a slightly elongated sphere (ovoid shape) or a flattened sphere on the distal side. This intra-procedural shape alteration fine-tuning feature may be useful to the operator in ensuring that additional clean margin tissue will be captured on the distal side of the target (carriage moves forward towards the end of a curved tip deployment phase), or equally importantly, for example, in flattening the sphere on the distal side (a carriage slides backwards at the end of the curved tip deployment phase), to avoid getting too close to sensitive tissue or structures on that side of the target, such as a chest wall, nerve, or major blood or lymphatic vessel. This ability to add another control to the final shape of tissue that may be isolated and excised is also an added safety factor of the device, and may also be useful in capturing clean margins of healthy tissue around an elongated target tissue, according to the present embodiments.

Figure 12:
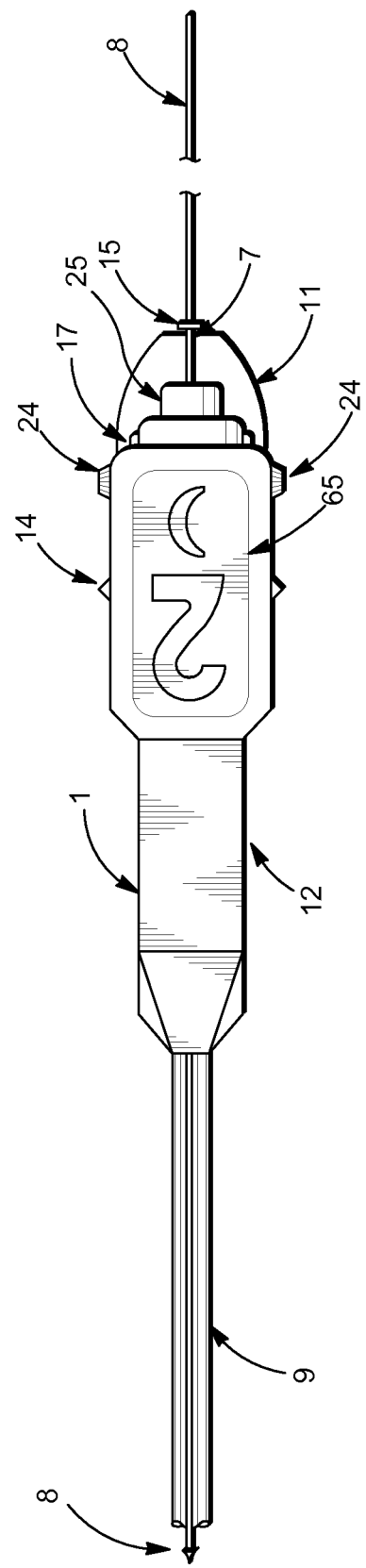
FIG. 12 is a top view of the device 10 according to one embodiment.

FIG. 12 illustrates a top view of the device of FIG. 10, according to one embodiment, showing the device 1, with the outer tube/barrel assembly 9, the central tube 7 passing completely through the device, a replaceable upper slide unit 12, and a handle/lower slide/power unit assembly 11. This figure also illustrates one exemplary layout of the ambidextrous controls that may be viewed from this perspective, including a vernier adjustment knob 24, an upper slide lock 17, a depth indicator 14, as well as a lock mechanism 15, which may also serve as a sealing mechanism for the end of the central tube 7 (with or without a locating wire or fiber optic cable passing through it to prevent release of fluids or other substances into the operating theater atmosphere), and a locating wire.

This view also shows a model designator area 65, where an upper slide housing has a model number and tip size/shape molded into it or otherwise affixed for easy reference by the operator in selecting an upper unit pre-loaded with a certain size and curved tip shape, as discussed under FIG. 11. Model numbers may vary by tip size and configuration of a gear drive that is matched to different tips, as will be discussed under FIG. 15. The model number of an upper unit would thus correspond to one of a listed series of upper unit models on a laminated chart for reference, supplied with the device in one of its embodiments, and the chart may comprise all of the parameters that would be applicable for each model number, including such information as total curved tip length when deployed, total central tube length for correlation to the graduations on the locating wires, the type of locating wire supplied with the upper unit model, the curved tip shape, and other parameters. Such an upper unit may be intended to be molded of a transparent (e.g., plastic) material so that the operator can actually see the movement of the internal mechanism, as desired.

Figure 13:
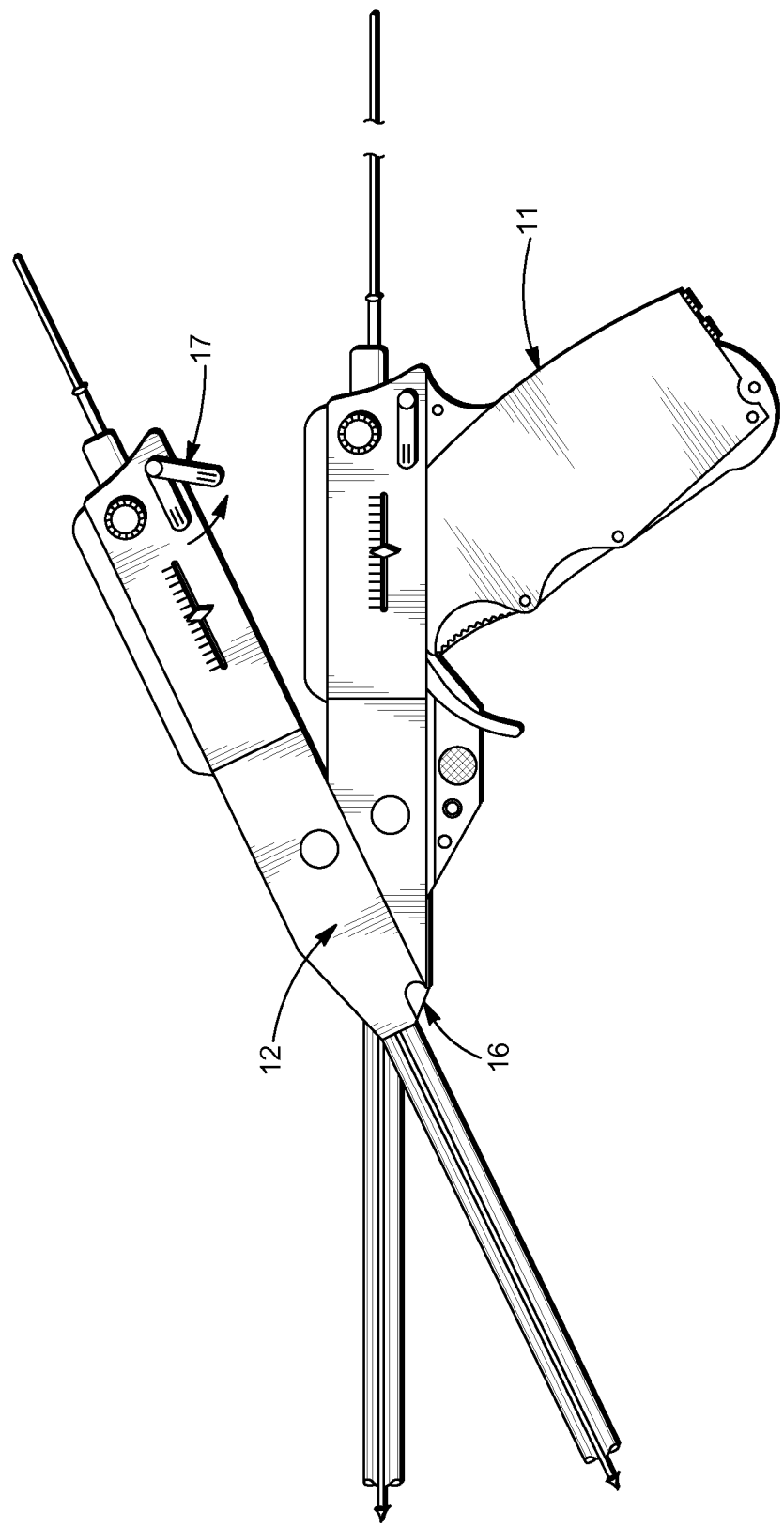
FIG. 13 is a side view of the device of FIG. 10, according to one embodiment.

FIG. 13 shows an upper unit hinge point tab 16, an upper unit locking lever 17 of an upper unit, and a lower handle/power/control unit 11 according to one embodiment. The ability to change out, intra-operatively if necessary, either an upper or lower unit(s) of the device illustrates a significant safety factor that may be built into this device. If there is failure of any part of a lower unit, it may be replaced and a replacement unit attached to an upper unit to allow the procedure to continue. If it is determined that curved tips 5 maximum diameter would be insufficient to completely enclose a target tissue or foreign body with clean margins all around it, the entire upper unit may be exchanged for one with pre-loaded rod elements and curved tips of a greater dimension (or vice versa for a smaller dimension, as the case may be), with several upper units available to the operator for selection during the procedure. Alternatively, the operator may have several of the devices 1 at hand, each loaded with tips of different dimensions or configurations, to be used as desired for different targets during the same procedure. Such a lower unit may be configured, as shown in FIG. 14, so that the only mechanical connection between an upper unit 12 and a lower unit 11 is the top of a motor/pinion assembly 31, which engages an upper unit gear drive automatically when an upper unit is locked down to a lower unit, and a sliding carriage link 47 (both of which are not shown in this illustration).

Figure 15:
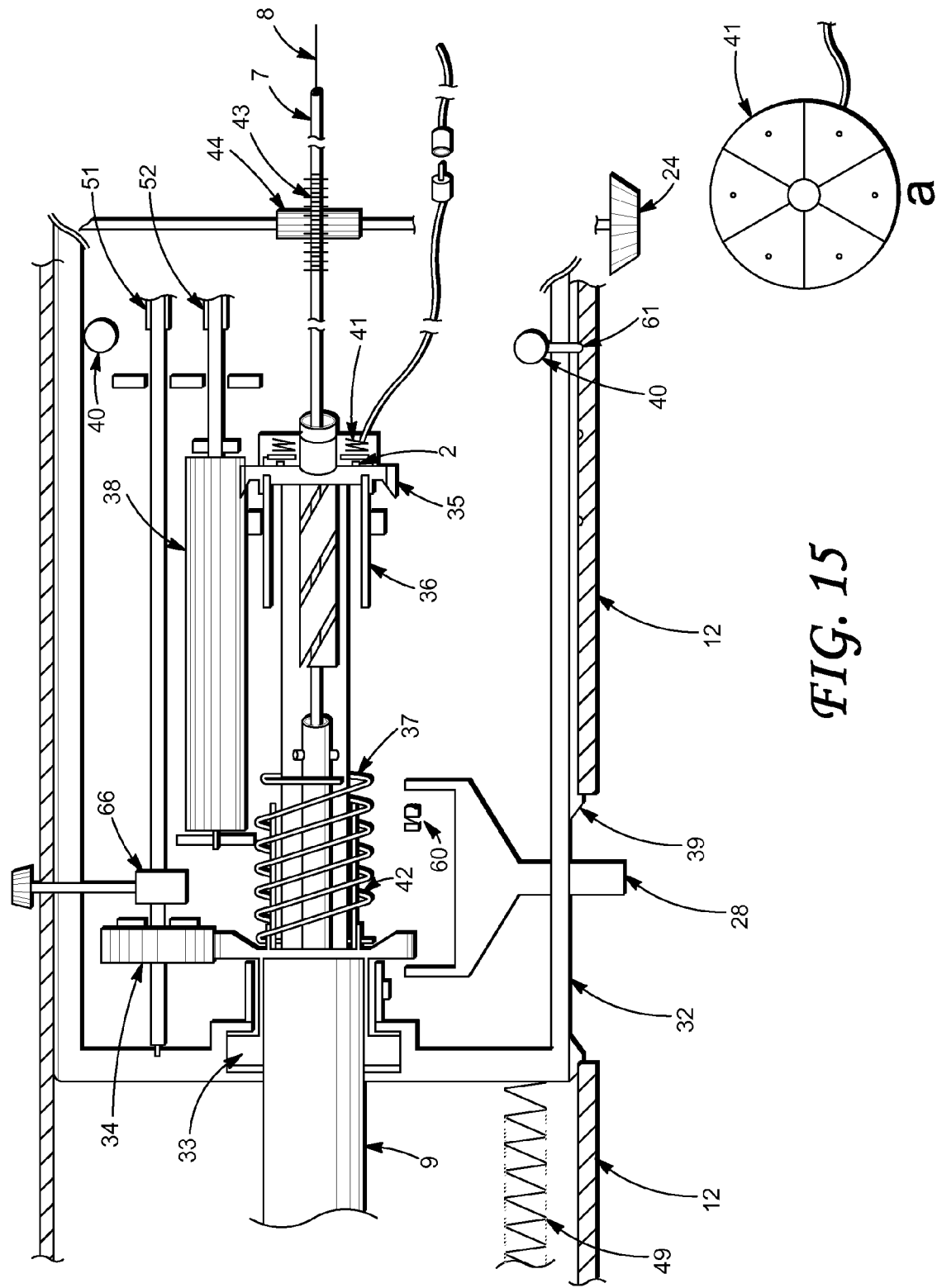
FIG. 15 is a top down view of an upper level of the device 1 of FIGS. 8 and 10, according to one embodiment.

This ability to change out either a complete upper unit or a complete lower unit also illustrates that a lower unit, at the least, may be re-usable, since no part of its structure actually enters the patient during the procedure, and as will be shown, in FIG. 15, the outer tube/barrel 9 and associated parts of the complete tip of the device may be readily and easily changed for a complete replacement unit as a sub-component assembly within the structure of the upper unit 11 of the device. This built in design feature allows for maximum flexibility and device cost effectiveness, as approximately 90% of the device may be configured to be re-useable from procedure to procedure, and 100% of the device may be configured to be recyclable at the end of its useful life. A lower unit 11, with a defect which may be limited, for instance, to a malfunctioning or worn out switch, may be returned for refurbishment with a replacement unit provided to the operator for use in the meantime. The refurbished unit may then be sterilized, packaged and ready for re-issuance for thousands of future operations, until its useful life had passed, at which time it may be disassembled and its parts recycled. A similar scenario may be envisioned for all of the subassemblies of the upper unit 12.

Figure 14:
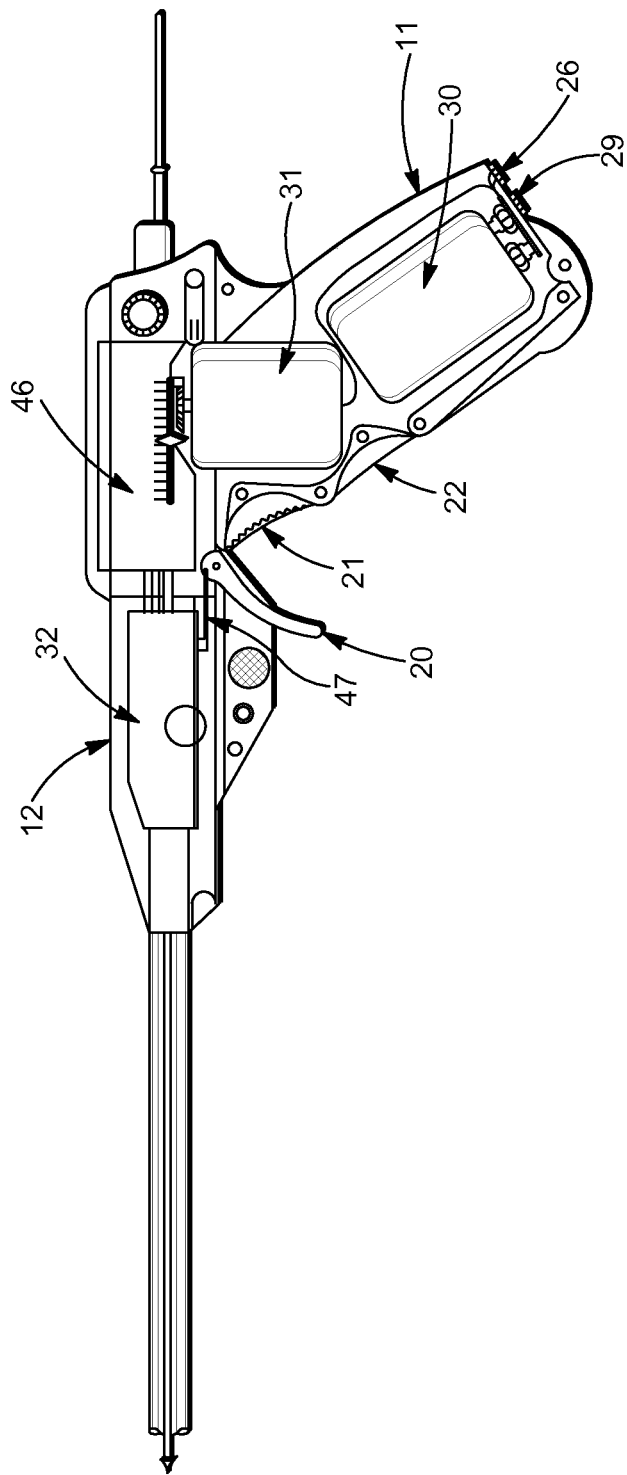
FIG. 14 is a side view of the device 1 of FIG. 10, according to one embodiment.

FIG. 14 is a side view of the device of FIG. 10, according to one embodiment, showing internal placement of a motor/pinion gear assembly 31, a battery power source 30, a lower unit external power supply jack 26, a transfer case 46 containing a drive mechanism that automatically engages and connects to a pinion gear of a motor/pinion assembly 31 when an upper unit 12 is dropped onto and locked to a lower unit 11, the internal placement of a self-centering sliding carriage 32, and a carriage slide link 47 engaging a sliding carriage 32 and a carriage slide lever 20. The battery source may be a readily available 9-volt rechargeable battery, which is useful for remote field operations, where a supply of batteries and a recharging station would answer all of the power needs for the device, in a simple embodiment, although other power sources may be envisioned, as may be an external power source. The motor may be a commercially available direct current unit, used for many purposes such as in model cars. These motors have sufficient torque for this purpose, are inexpensive, and eliminate the need for reversing gears in a simple instrument, since reversing current flow to the motor reverses its direction, such as controlled by switches 21 and 22 of the device shown in the embodiments shown in FIGS. 8 and 10. Also shown is a battery compartment cover lock 29. Details of the internal mechanisms of a sliding carriage 32 and a transfer case 46 may be found in FIGS. 15 and 16, respectively. This figure also illustrates the simplicity of replacing a motor/pinion gear assembly with, for instance, a purely mechanical drive unit, such as a wind-up motor, in place of a DC current motor shown in this figure. Associated controls in such an embodiment of the device would in that case be limited to the essential mechanical linkages (such as a collar brake to start and stop a motor and a separate reverse idler gear to compensate for a one-way rotation of a spring powered motor) to a purely mechanical motor/pinion gear assembly 31, which would be rod tip extension/rotation switch 21 and rod tip retraction/rotation switch 22, and in that case the device would still perform its basic functions (surround a target, capture it, immobilize it, isolate it and retrieve it), as will become apparent with reference to FIGS. 15 and 16.

FIG. 15 shows the working mechanical/electrical details of a self-centering sliding carriage subassembly 32, according to one embodiment. First shown in FIG. 14 above. FIG. 15 shows the self-centering sliding carriage subassembly 32, configured to house a principal driving mechanism of a device tip subassembly, and to slide axially on its side rails 39 in matching grooves of an upper unit 12 housing. A self-centering mechanism of such a carriage housing may be based on four springs 49 (of which only the lower left spring is shown) locating it to its normal position within an upper unit 12. The axial movement of such a carriage on its slide rails may be controlled by a carriage slide lever 20, as shown in FIGS. 10 and 14, and a connecting carriage slide link 47, as shown in FIG. 14, engaging a carriage lever pivot sockets 40 in the base of a carriage housing, as shown in this figure. A carriage, according to one embodiment may contain most of the mechanical drive elements, and such a carriage and its contained elements may be configured to carry out all of the intended motions that would affect the movement of curved tips, an outer tube/barrel assembly and the actions for target tissue or foreign body isolation/part-off and excision. Each of the elements contained within such a sliding carriage housing may be configured to be dropped in with locking snap-on tabs or plates holding them in their intended positions, which may be located by columns or pylons molded into the carriage housing, for ease of assembly and manufacturing, as well as replacement as discussed further below. A carriage may be replaced in an upper unit 12 as a whole subassembly or just a device tip subassembly, contained within a carriage subassembly as discussed below, may be replaced between procedures. This may limit the need for replacement and sterilization of the entire device between procedures, and any number of replacement sterilized subassemblies (carriage or device tip, preferentially the latter only) may be used with the same upper unit 12 and lower unit 11 of the device.

The driving components located within such a carriage housing may comprise an outer tube/barrel assembly 9 proximal end press fit into an outer tube collar/gear 33, and through which pass rod elements 2 (out of the proximal ends of their tube chambers, which are press fit into holes in an outer tube collar gear 33) and a central tube 7, which emerges from its sleeve that ends at a gear 33 like tube chambers. The collar of this element may be configured as a thrust bearing within its housing, as shown, and may positively lock the device tip to a carriage 32, and thus to an upper unit 12. When such a carriage 32 moves axially forward or backward, it moves the tip of the device as well, which may serve to fine tune the movement of deployment of curved tips from their tube chambers, thus altering the three dimensional shape of a target to be isolated and/or excised, as discussed relative to FIG. 11 above. This figure illustrates the very simple and robust manner in which a carriage may accomplish this action, in conjunction with a slide lever 20 and linkage 47. If such a slide lever 20 of FIG. 11 is locked all the way in its extreme forward position, the carriage slide link 47 (shown in FIG. 14) will engage through a carriage lever pivot socket into a depression in an upper unit (carriage lock 61, shown in FIG. 15), thus locking a carriage 32 rigidly within an upper unit 12. Additional locking points may be provided between a carriage and an upper unit housing to enable the operator to lock such a carriage at its forward-most, middle and after-most positions by a second external button lock 63, shown hereunder relative to FIG. 18.

In this configuration, rod elements 2 may extend through holes in an outer tube collar/gear 33 and may be positively anchored at their proximal ends to and through a rod element clutch gear 35, with their proximal tips extending through that element to contact an RF energy distributor contact plate/wiring/housing subassembly 41. The RF energy distributor contact plate may be kept in contact with the proximal ends of rod elements 2 by springs within that subassembly housing, which does not rotate, as shown in this figure. The RF energy distributor contact plate is also shown in FIG. 15A in the lower right hand corner of the illustration, showing that its contact face may be segmented as well, with one segment for each rod element 2 contained in the device tip (outer tube/barrel 9 subassembly), represented by the dots in each segment, as though rotation has been frozen for an instant for illustration purposes. Power to all segments may be provided by attaching a wire to the outside continuous conducting circumference of a contact plate delivering power to all segments, as shown. As the proximal tips of rod elements 2 pass over an RF energy distribution plate, the contact allows the RF energy to pass to curved tips of rod elements, if selected by a switch 18 of FIG. 11, and if either of the control switches 21 or 22 is actuated. If an RF distributor contact plate is segmented as shown, with insulated lines between segments on its face, the RF energy, which may be of the pulsed type, the rod elements will be additionally pulsed as they pass over each segment in rotation. This pulsing action may assist the RF energy's action by initializing and maintaining the arc of energy between rod element tips and the tissue encountered in their path.

Figure 16:
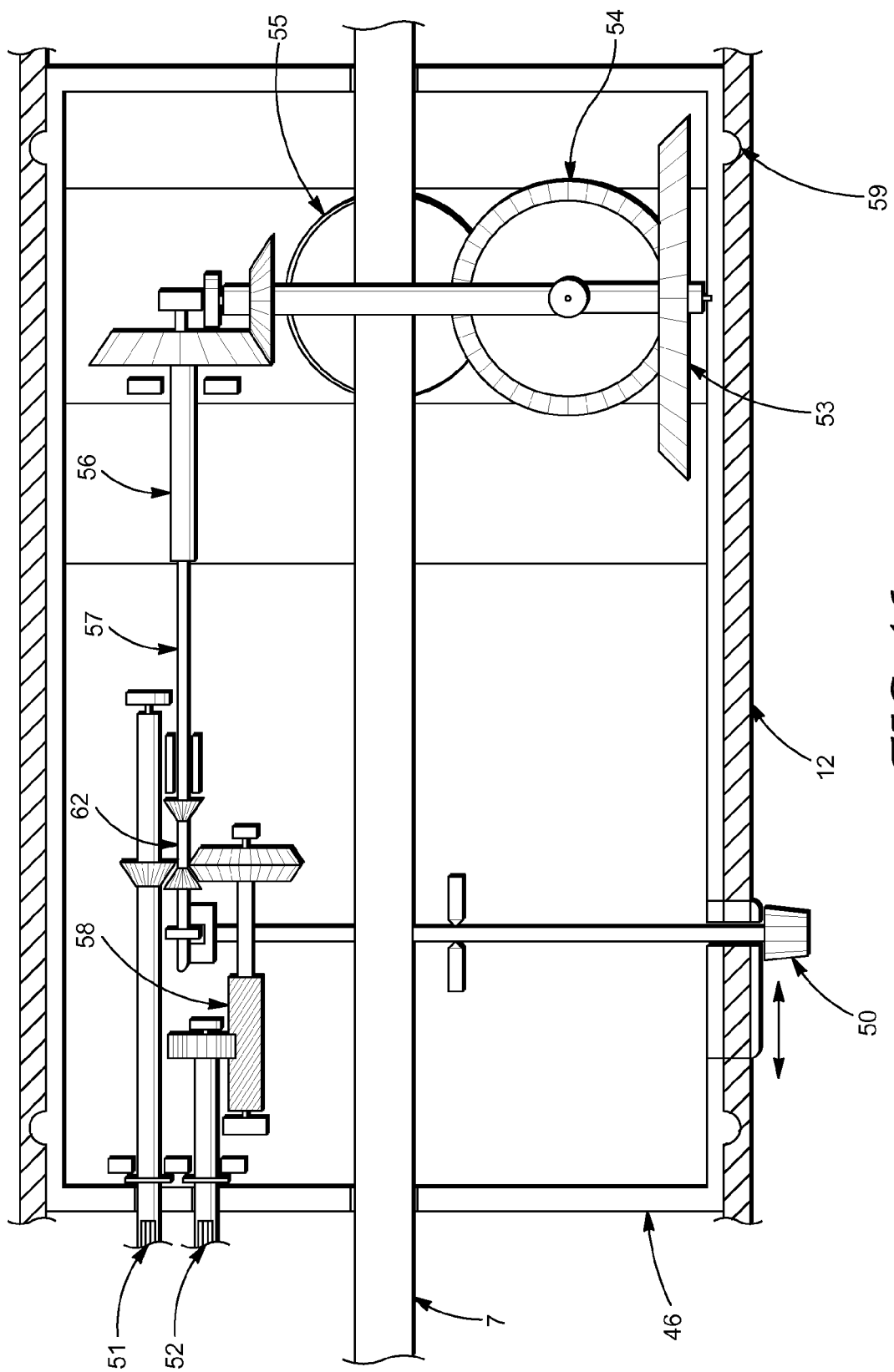
FIG. 16 is a top down view of the transfer case and driving mechanism within the upper unit of the device of FIGS. 8 and 10, according to one embodiment.

The following elements of a carriage subassembly list for illustration purposes the important elements of one embodiment of the device of FIG. 8 or 10. This discussion of one embodiment assumes that a motor/pinion assembly is connected to a sliding driveshaft 52 via its own worm gear pinion/driving gear (as shown in FIG. 16) on a driveshaft 52; a self-centering sliding carriage 32 with its associated parts (elements 40, 61, 39 and 49) as the housing for this minimized subassembly, an outer tube collar/gear 33, an outer tube gear sleeve 42, a tension spring 37 whose principle function is to balance the exit forces of the curved tips from their tube chambers and to assist gear 35 to induce the curved tips of the rods to re-enter their tube chambers when retracted by giving an extra force to a clutch gear 35 as it returns axially in a proximal direction. It is anticipated that the curved tips, because of their spring-like nature, may tend to want to exit their respective tube chambers of their own volition once they have been initially extended forward as a result of the action of gear 35, and once that starts, gear 35 may be in a position of having to hold the rod elements back as opposed to having to push them forward. A tension spring 37 may be provided to balance that tendency and to also serve as an additional retrograde assist to gear 35 as it travels axially back to its rearward-most position and drags the curved tips back into their tube chambers.

Also comprised in this embodiment for the subassembly within a carriage are a rod element gear casing 36, a rod element clutch gear 35, a micro-switch 60, a radiofrequency (RF) energy contact plate/housing 41, a rod element pinion gear 38, and a sliding driveshaft 52. These elements work together to provide the desired action on the outer tube/barrel assembly 9 and rod elements 2. The direct drive to a rod element clutch gear provides low speed/high torque to that gear, since it is anticipated that torque requirements may be a significant limiting factor. In this configuration, the outer tube pinion gear 34, its sliding driveshaft 51, and gear lock 28 may each be unnecessary, and may be considered optional. By eliminating gear 34 as outlined above, an entire transfer case, as shown in FIGS. 14 and 16, may be minimized or eliminated as well, as is discussed below.

Examining the principles of movement of the outer tube collar/gear 33 in relation to the rod element clutch gear 35 yields the following. As shown in FIG. 15, the two gears are shown in exploded view and have not been assembled, for ease of analysis of their functions. The actual assembled configuration for rod element clutch gear 35 may be over a central tube of outer tube collar/gear 33, with the grooves of the shaft of rod element clutch gear 35 engaging the two pinion dowels shown approximately midway on the shaft of the collar/gear 33. According to one embodiment, these two pinion dowels may take the form of ridges molded into and spiraling around the shaft of a tube collar/gear assembly to match the pitch and ride in the grooves of a rod element clutch gear 35. This embodiment may effectively prevent stress shearing of the two pinion dowels, as a great deal of torque loading may be present at these two points, and would also provide a long-wearing and very robust structure. One limiting factor for these spiral ridges may include the friction load that they will bear as they ride in the grooves of a clutch gear 35, but as this mechanism may be configured for low speed/high torque, it is assumed that either a surface treatment or lubrication be carried out. The rod element proximal ends may be embedded through the base of a rod element clutch gear 35, according to one embodiment, and may thus be in contact with an RF energy contact plate 41, whose wiring may be connected to a plug socket or sliding contact plate an the rear bulkhead of a sliding carriage 32 housing. Such a rod element gear casing 36 may be configured to slide over an outer tube gear sleeve 42, and a tension spring 37 may be configured to surround a rod element gear casing.

When rotational force is applied to a sliding driveshaft 52 from the motor, it will turn rod element gear pinion 38, which will turn rod element clutch gear 35. As this happens, the torque will be applied to the grooves of that gear to the pinion dowels (or spiral ridges) on the shaft of an outer tube/collar gear 33. As a result, the rod element clutch gear will begin to rotate around the shaft of an outer tube/collar gear and advance laterally forward, twisting itself and the rod elements, which are also moving forward with a clutch gear, around that shaft, in a motion similar to that explained in FIG. 5, and in fact, clutch gear 35 takes the place of rod actuator element 4 of FIGS. 1 and 5. As the rod elements are twisted (they must twist since gears 33 and 35 would not be rotating with the same speed) and moved axially forward (to the left in the illustration), this action is transmitted to the distal extremity of the rod elements, causing curved tips 5 to extend, deploy and rotate around a target (this action is not shown here, but illustrated in FIGS. 1 and 5). As the rod element clutch gear is driven by a pinion gear 38, it slides forward along that pinion gear. As it receives the rotational force from that pinion gear, it also acts on the pinion dowels of an outer tube collar/gear 33, and that gear in turn starts to rotate the entire outer tube as the rod elements themselves are twisted around its axis. The ratio of outer tube rotation to rod element axial deployment/twisting rotation may be a function of the angle of the groove of a rod element clutch gear 35 engaging the pinion dowels of an outer tube collar/gear 33 as well as the resistance of rod elements to twisting and frictional forces acting on an outer tube/barrel. The torque imparted to an outer tube may be increased if the grooves of the rod element clutch gear are steeper, or more nearly parallel to the central axis of that portion of a clutch gear. If the grooves are of shallower pitch (i.e., closer to perpendicularity to the central axis of a clutch gear), less relative torque may be applied to an outer tube collar/gear. The actual degree of the pitch of the slots in a rod element clutch gear may thus determine how much an outer tube/barrel assembly will rotate as the rod elements are pushed axially and rotate on their axes by twisting around the shaft of a rod element clutch gear 35. This ratio may be fine-tuned at will.

Another significant ratio is that of axial travel of a clutch gear 35 toward gear 33, and the total amount of rotation that wrapping rod elements around its shaft will be. A simple way of visualizing the significance of this ratio is that the total distance travelled axially forward by a clutch gear 35 must end with rod elements being twisted so that they rotate on their axes enough to bring their curved rod tips to at least 180 degrees from the direction that they were initially pointing in their tube chambers, but not much more than that, if any. This action, as previously discussed, would allow the tips to travel out and around a target tissue or foreign body. In actual fact, curved rod tips may not have to travel a full 180 degrees, and may also travel over 180 degrees, if desired, according to embodiments. The nominal target for rotation while penetrating forward for the rod tips may be, for example, approximately 185 degrees (to compensate for twisting drag forces on deployed rotation or to allow the tips to cross over each other at the distal ends, if they are of the configuration shown in FIG. 7A), although other targets for rotation may be found to provide utility within the present context. The total length of travel of such a clutch gear 35 in forward travel (which is primarily determined by the total length of the matched curved tip of a rod element selected), the pitch of its grooves, the total friction load of the mechanism, the torque delivered to a clutch gear, the tension spring resistance, an outer tube frictional resistance to rotation, the density of the tissue expected to be encountered by the curved tips in deploying (tip penetration/revolution), combined rod element flexibility, and other factors may be taken into account in fine tuning the operation this subassembly, as those of skill in this art may recognize. For instance, the grooved shaft of gears 35 and the ridged shaft of gear 33 may be very long with a very shallow twist, to allow rod elements plenty of length to twist/rotate around a clutch gear 35 shaft at full forward lock. The longer that distance is, the easier it will be to twist the rods and the easier it will be to assemble the device during manufacture.

The outer tube/barrel assembly may not necessarily be round in cross-section, and may have ridges, spirals or other surface treatment to assist in frictional drag or to lessen it. The shafts of penetrating rods may be of "X" or spiral cross-section along their shafts, for example, or thinner in the area expected to be twisted, or have other cross-section that allows twist, but resists angular deflection when loaded axially, or have varying cross-sections along its length. In any case, the use of this gear arrangement described herein, is rugged, easy to assemble, inexpensive, and most importantly, assures that the functional motions described herein—those of simultaneous rod tip axial penetration, deployment, rotation and revolution out and around a target tissue or foreign body with clean margins around it—may be carried out. When a rod element clutch gear has reached the end of its forward travel, its gear casing 36 may came into direct contact with an outer tube collar/gear 33 over its outer tube gear sleeve 42, compressing a tension spring 37 as it approaches gear 33. Once it is in direct contact, it can go no further forward, (the curved tips 5 of the device are now at their fully deployed stage around a target, are pre-loaded with torque, and cannot rotate further) and from that point all of the driving torque applied to a clutch gear 35 may be transmitted directly to an outer tube collar/gear 33, driving it in rotation in the direction of its own rotation. At that point, it also trips a micro-switch 60, which cuts off power to the first detent of a switch 21 of FIG. 11, as discussed under FIG. 11. If that switch 21 is pressed to its second detent, a micro-switch 60 may be disabled, allowing a clutch gear 35 to continue driving a gear 33 until the switch 21 is released. In this latter mode (switch 21 pressed all the way to its second detent), gear 35 will drive gear 33, an outer tube/barrel assembly 9 will rotate, and a target enclosed by the fully deployed curved tips will be parted-off from the surrounding tissue as the edges of the curved tips carve the spheroid shape enclosing a target.

If a retraction/rotation switch 22 of FIG. 11 is activated, it drives rod element gear pinion 38 in reverse. A micro-switch 60 would not be connected to switch 22, so it may be actuated at any time, for instance in alternation with switch 21 as the operator is positioning the device in proximity to a target and making short, incomplete penetration/retraction movement of the curved tips to optimally place the device, and perhaps verify that placement with image guidance devices, before continuing the procedure. If such a rod element clutch gear is in its rear-most position (rod tips not deployed out of their tube chambers around a central tube), such a rod element clutch gear 33 may be configured to drive an outer tube collar/gear 33 in reverse rotation, since it will be impossible for gear 35 to move any farther to the rear, and all of its torque moment is transmitted to gear 33 through the pinion dowels on its shaft. This reverse rotation of an outer tube/barrel assembly may be used as a standard device penetration from the percutaneous entry point to final position to a target. The rotation of an outer tube/barrel assembly 9 en route to a target site has already been discussed relative to FIGS. 7A-7D above. Such rotation may assist penetration using the principle of compound friction overcoming simple friction. With reverse rotation, the rod elements curved tips are prevented from accidentally deploying, since a clutch gear is driving in reverse and actually locking the rod tips in their respective tube chambers. Retraction/rotation switch 22 of FIG. 11 and other figures may also be used to retract rod element curved tips back into their tube chambers, if a rod element clutch gear 35 is already at its forward-most position, locked up against a tube collar/gear 33. This switch would also be the one to use if the curved tips have been deployed or partially deployed by action of a switch 21, and it is desired to retract the tips for repositioning of the device, or for release of the collected target after the procedure is finished, either in single insertion-single retrieval, single insertion-single isolation or single insertion-multiple isolation mode of the device, according to one embodiment.

Also shown in FIG. 15 are a separate higher speed/lower torque optional outer tube pinion gear 34, a driving gear 33, and its associated sliding driveshaft 51, which may act in concert with gears 38, 35 and 33 at the same time, or separately from gears 38 and 35, according to one embodiment. Control elements 19, 23 and 50 of FIG. 12 may be dedicated to this outer tube pinion gear's action in concert with the gearing of a transfer case discussed and illustrated in FIG. 16. An alternative use for pinion gear 34 with a shortened driveshaft 51 may be to include with this subassembly a tension drag collar 66 and external control knob, in which case the driveshaft would not necessarily be driven. This tension adjustment mechanism may be configured to increase drag on gear 33 in relation to the relative movement of gear 35, and may limit gear 35's tendency to impart too much rotation on gear 33 during forward deployment of the rod elements, and may be controlled by the operator via an external knob. It is anticipated that this fine tuning drag or tension feature may find particular utility with low density tissue such as fatty tissue encountered by the tips of the device, which may tend to upset the balance of the relative action of gears 33 and 35, since there would be less external friction drag on an outer tube/barrel assembly and less resistance to penetration of curved tips through such low density tissue, and thus tend to increase the rotational factor of an outer tube/barrel assembly and gear 33 with relation to the movement of gear 35. A simple gear lock mechanism 28 may be used when a clutch gear 35 is in its foremost position against gear 33. This may be configured as an optional safety feature to ensure that these two gears do not twist themselves away from each other when the curved tips are fully deployed around a captured target and thus accidentally let go of the target during extraction. In actual fact, use of this safety feature is a redundant mechanism, since a worm drive pinion for gear 35 (shown in a transfer case of FIG. 16), coupled with a worm gear-like quality of a gear 35's slotted shaft acting on the pinion dowels of a gear 33 effectively lock gears 33 and 35 together in whatever position relative to each other that they are driven to by one single gear—the rod element pinion gear 38. This keeps the rod elements from untwisting and trying to drive gear 35 in reverse, and contributes to the torque loading experienced by each rod element in its fully deployed state which, in turn, makes its curved tip edges more rigid in plane and increases curved tip side cutting efficiency.

Finally, although it is shown located at the rear of upper unit 12 of FIG. 11, the details of a central tube vernier knob 24, a central tube pinion gear 44 and a central tube rack gear 43 are shown towards the right of a carriage. A turning knob 24 may be configured to act on a rack and pinion mechanism to move central tube 7 in relation to the device, allowing the tip of central tube 7 to advance to or into and retract from a target, and if locked to a locating wire 8 by a central tube/locating wire lock 15 of FIG. 11, a vernier knob 24 will advance or retract both central tube 7 and locating wire 8, relative to the device. This latter action may be taken, for instance, if the operator wishes to remove the device and a target from the body with both a locating wire and a central tube in exactly the position they were relative to the target just before removal of the target from the body, which also aids in immobilizing the target during extraction. A knob 24 also may be configured to actuate the external depth indicator 14 on the outside of an upper unit 11, as shown in FIG. 11. It should be noted that the central tube may run through all of the main driving elements (gears 33, 35, tension spring 42 and RF energy assembly 41, a transfer case of FIG. 16, and other elements) and may not be affected by any relative motions of any of these elements.

In this FIG. 15, the following elements within a sliding carriage subassembly 32 may be easily replaced, according to one embodiment, without replacing any other parts of an upper unit 12 or lower unit 11; an outer tube/barrel assembly 9 (with rod elements 2 and tube chambers 3, and a central tube 7) and a subassembly comprised of gear 33 with attached sleeve 42, tension spring 37, gear 35 with attached casing 36, and RF energy contact plate/housing 41. This essentially constitutes the entire forward tip of the device, and this ability to change just these elements as a matched subassembly allows for several key advantages related to this embodiment. Such advantages may include, for example, the ability of an operator to change out the entire tip of the device for another tip with different curved tip dimensions or characteristics, cost effectiveness of the whole device because approximately 90% of the whole device is reusable, environmental friendliness because 100% of the device is recyclable, and so on. As noted above, the length of axial travel (and therefore the lengths of their shafts) of gears 33 and 35 relative to each other may be matched to the set of rod elements that they drive, especially as related to the curved tip length of those rod elements. According to one embodiment, when gears 33 and 35 are at their closest proximity to each other and locked into that position (gear 35 all the way forward against gear 33), the curved tips of the rod elements should be fully extended and rotated (fully deployed). When gears 33 and 35 are as far from each other as possible (gear 35 fully retracted), the very tips of the curved tips of the rod elements should be fully retracted into their individual tube chambers, in loaded or at-rest position. This is why it may be desirable to be able to change device tips as a subassembly to attack different sized target tissues or foreign bodies in the body. The sliding carriage housing may allow for these components as a subassembly to be dropped in place and locked down, making change out of this device tip subassembly relatively simple.

It can also be envisioned, by one skilled in the art, that other arrangements or designs for a device tip main driving subassembly are possible, such as belt drives, sun/planetary gears/ring gears or other gear arrangements, perpendicular tabs from a rod element shaft to a central spiral groove that rotates them on their own axes as they are advanced axially, and other operating mechanisms and controls. Such alternative designs should be considered to be within the scope of the embodiments shown and described herein.

FIG. 16 shows a top down view of a transfer case 46 in one embodiment, located within upper unit 12 of the device in this embodiment and locked to it by locating tabs 59, containing various drive gears and clutch mechanisms, configured to transfer rotational movement from a motor/pinion assembly 31 to the sliding driveshaft(s) 52 and/or 51, and thus to the sliding carriage mechanism of FIG. 15, all of which are located to allow central tube 7 to pass axially through this driving mechanism unencumbered by a drive mechanism. Placement of this transfer case within upper unit 12 is outlined in FIG. 14, and the three-dimensional shape of that transfer case outline is replicated in this illustration for ease of understanding. This subassembly within an upper unit 12 may be configured such that it may be dropped down onto a motor/pinion assembly and engaged through pinion aperture 55 with idler gear 54, in the device outlined in FIGS. 8 and 10, and as shown in FIG. 13, according to one embodiment. The idler gear 54 may be configured to engage a transfer gear assembly 53, which may be configured to engage a common drive/gear selector assembly 56 with its sliding driveshaft 57 and sliding selector gear unit 62. A sliding selector gear 62 may be actuated by an outer tube rotation-only selector switch 50. An outer tube rotation-only switch 50 was shown on the device in FIGS. 8 and 10, and its action as a lever to selector gear 62 on the sliding driveshaft 57 is shown by the double headed arrow next to switch 50 on this figure.

This embodiment shows the ability of selector gear 62 to act as an idler gear between sliding driveshaft elements 51 and 51, which extend forward to the sliding carriage of FIG. 15. In this configuration, selector gear 62 chooses either to drive both driveshaft elements simultaneously (meaning that rotational power is sent to both gears 33 and 35 in a sliding carriage subassembly of FIG. 15) or only driveshaft 52, which powers gear 35 of sliding carriage subassembly of FIG. 15 through worm gear 58 in this transfer case subassembly. As discussed relative to FIG. 15, this worm gear 58 acts as a pinion gear, along with the slotted shaft of gear 35 acting on the shaft of gear 33, effectively lock gears 33 and 35 together in whatever relative axial position they are to each other when rotational power is interrupted (motor shut off). This action interrupts and freezes the position of the curved tips 5 of rod elements 2 relative to the mouth of their tube chambers 3 at any time the operator desires by releasing switches 21 or 22, as outlined previously. Other embodiments of a transfer case in which only one or the other of driveshafts 51 and 52 is powered may be devised if such functionality is desired. As noted relative to FIG. 18 below, all or most of this transfer case may be eliminated or minimized in an embodiment, and further, many different configurations that would comprise the use of belt drives and pulleys or other arrangements may be envisioned as mechanical equivalents to that shown and described herein, which are to be considered to fall within the scope of the present embodiments.

Figure 17:
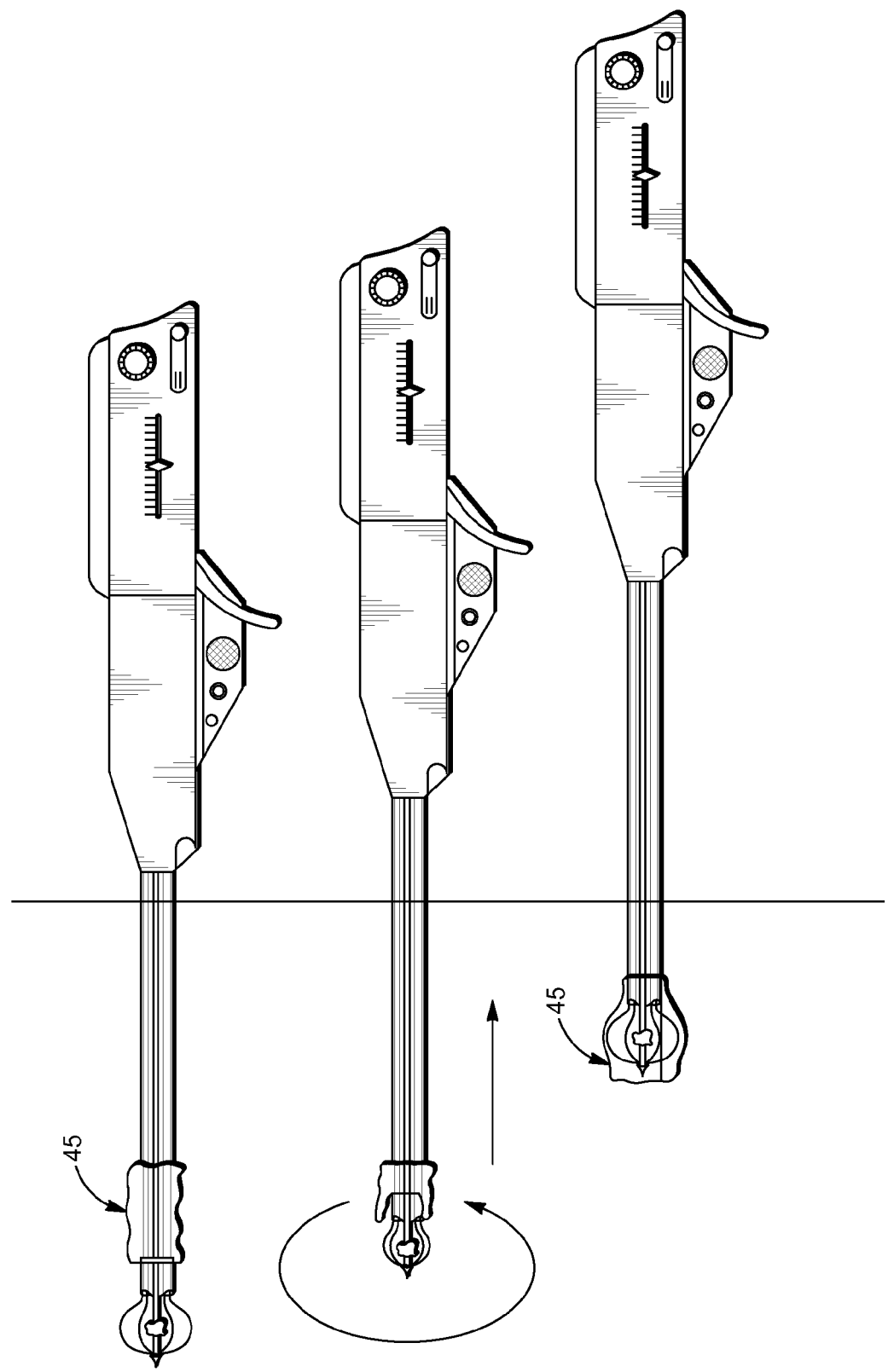
FIG. 17 illustrates three perspective views of one portion of a device of FIGS. 8 and 10, according to one embodiment.

FIG. 17 shows three side views of an upper unit and device tip, according to one embodiment, in three stages of exiting a target site while withdrawing a captured and excised target in a fully deployed tip basket. The vertical line represents an exemplary percutaneous entry point and the device in the top view shows a simple fabric sleeve or bag 45, which may be attached to the device tip at its forward end by either a circle clip, an "O" ring in a groove on an outer tube/barrel 9, or other means, such as adhesive. As the device is withdrawn, preferably with simultaneous rotation in either direction of an outer tube/barrel as shown, with its captured target, a sleeve/bag element 45 will tend to fold over and wrap itself around the captured target in the formed tip basket as it turns itself inside out, which may thus accomplish three important functions, among others:

(1) to decrease friction between a captured target and the tissue through which it must pass on its way out of a percutaneous incision;
(2) to give an even more positive grip of the curved tips on a captured target, and
(3) to prevent contamination of the healthy tissue on the extraction path to a percutaneous incision point.

The sleeve/bag element 45 may be constructed of a variety of commercially available material, such as nylon weave, Tyvek®, M5®, a high modulus thin film, a non-woven material or other material that resists tearing and is ultra-thin and flexible. It is not necessary that the sleeve/bag element 45 be resistant to heat from, e.g., an RF energy source, since its normal position intra-procedure is along the shaft of an outer tube/barrel 9. If the device is used in any of its single insertion-single isolation, single insertion-single isolation or single insertion-multiple isolation modes, a sleeve/bag element 45 may be present or omitted, as desired by the operator. The sleeve/bag element 45 may be given a variety of interior/exterior surface treatments to either reduce friction (inside surface which when deployed becomes the outer surface) or to increase it (outside surface which becomes inside surface when deployed, and thus grips the captured target, the sleeve bag/element 45 may also have special forms, features or devices incorporated into it to elute a number of drugs, anesthetics or other biologically active substances to the traversed tissue, either on the way to a target site or upon leaving it. A sleeve/bag element 45 may also be attached to a locating tube 10, as shown in FIG. 7A, through which the device 1 is inserted to approach the target tissue site, and given simultaneous withdrawal of the locating tube 10 and the device 1, the sleeve/bag element would deploy around the target tissue as described above and below. This latter procedure would allow for multiple replacement locating tubes with attached sleeve/bag elements to be used with a single device 1 intra-procedurally.

Figure 18:
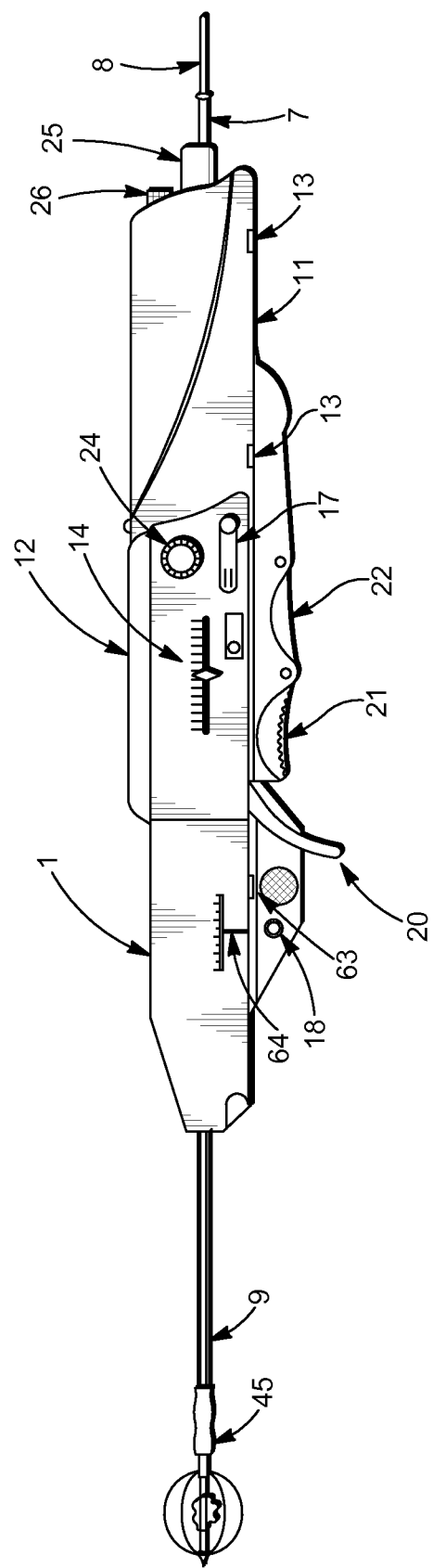
FIG. 18 shows the device of FIG. 8 illustrated to approximate relative scale, in one embodiment, with added external button lock element as well as external carriage position indicator, according to one embodiment.

FIG. 18 shows a device 1, according to one embodiment, with essential controls and features in a simplified form. In this embodiment, the controls have been limited to an RF power switch/indicator light 18, a carriage slide lever 20, a penetration/rotation switch 21, the retraction/rotation switch 22 and a central tube vernier knob 24. Also shown are an optional carriage lock button 63 and an external carriage position indicator 64. According to this embodiment, a motor/pinion assembly 31 may occupy the space of a transfer case 31 (as shown in FIGS. 14 and 16), and the pinion of a motor/pinion assembly may be a worm gear drive, as opposed to a bevel gear shown in FIG. 14, with a direct link to sliding driveshaft 52 to drive a rod element gear pinion 38, as shown in FIG. 15. As described relative to FIGS. 15 and 16, the use of a worm gear pinion for the drive mechanism of a sliding driveshaft 52 may obviate the need for a gear lock mechanism 28 of FIG. 15, since a gear driven by a worm gear cannot itself normally drive a worm gear. FIG. 18 also shows an outer tube/barrel assembly 9 which also shows the curved tips 5 fully deployed around tissue containing a target. In this illustration, it may be assumed that the final rotation/part-off has occurred, and that an outer tube/barrel assembly will be rotated, as the device is withdrawn from the body. As this occurs, either with or without rotation of the outer tube/barrel assembly, an outer tube capture sleeve/bag 45 may be configured to unfold as shown in FIG. 17, wrap itself around a curved tip formed basket and the captured target may be removed from the body for delivery to the pathologist in a sterile container. Finally, as described relative to FIG. 4, locating wires that may be supplied with this device may feature graduation marks along their length, thus enabling the operator to read the exact distance between the tip of the locating wire and the tip of a central tube directly off the proximal end of a central tube. The operator may also deduct the distance between the tip of a central tube and the tip of the device (tips of the tube chambers) from reading the carriage position indicator 64 and a central tube position indicator 14. This information may be of vital importance in correlating a target obtained with the pre-procedure target observed.

According to embodiments, various components, such as an outer tube/barrel assembly (device tip), that will briefly be placed into living tissues may be formed of or comprise biocompatible materials such as stainless steel or other biocompatible alloys, or may be made of or coated with polymers and/or biopolymeric materials, or any other material combination as needed to optimize function(s). For example, penetration/cutting elements may be made of or formed by hardened alloys or carbon composite and may be additionally coated with slippery materials to optimize passage through living tissues of a variety of consistencies and frictions. Some of the components may be differentially surface-treated with respect to adjacent components. A sleeve/bag system may be made of or comprise multiple types of material, since it is not exposed to the RF-generated heat and serves its purpose once such RF use has ceased, if used at all, according to one embodiment. The various gears may be made of or comprise any suitable, typically commercially available materials such as nylons, polymers such as moldable plastics and others. If used, a motor powering the various powered functions may comprise of a typical, commercially available electric DC motor, such as are commonly found in other medical devices. The handle (lower unit) and upper unit of the device may likewise be made of inexpensive, moldable plastic or other suitable rigid, easily hand held material and the handle may be configured in such a way as to make it easily adaptable to one of any number of existing guiding platforms such as stereotactic table stages. The materials used in the device may also be carefully selected from a ferro-magnetic standpoint such that the instrument may be compatible with magnetic resonance imaging equipment, which are commonly used for biopsy procedures. The vacuum/delivery assembly components may comprise commercially available syringes and tubing, for connecting to the instrument's common connection port, along with easily available reed valves for switching between suction and emptying materials such as fluids, which may be suctioned by the vacuum components. The materials collected by the instrument in this manner may then be ejected into an additional external, yet portable liquid storage vessel connected to the tubing of the instrument for discarding or for safe keeping for analysis and testing. The relative or absolute sizes of the individual components described herein may be matched to the intended use of the device. Therefore, no implication of relative or absolute sizes for any component or for the device in its embodiments should be inferred from the depictions or descriptions herein.

The power source may be an external commercially available transformer to DC current, approved for medical device use, and phlugged into a provided socket in the device, or may be an enclosed battery of any suitable voltage/current that is readily available commercially. The battery may be of one time use and recyclable or may be of the rechargeable variety. The power source may, according to one embodiment, comprise a wind-up spring-driven motor or in a very simplified embodiment, be entirely manually driven, with appropriate minimal changes to the device to accommodate such a power source.

Advantageously, embodiments are minimally invasive both externally (entry into the body through a percutaneous procedure) and internally. Indeed, the operator has the ability to reposition the tip by withdrawing the penetration elements within their delivery tubes and redeploying from another angle or position, with resulting minimal surrounding tissue damage since the points of the penetration elements follow a predictable curve and are not slicing or parting-off tissue until subsequent stages. Only when the operator is satisfied as to the amount of tissue that will be captured by final deployment and spatial placement of the penetration elements, for example to obtain cleaner margins on one or more sides of the target tissue, or for clearance in relation to surrounding sensitive structures, such as a chest wall, is it necessary to make the final decision to pursue subsequent stages, such as final part-off capture, collection and retrieval of the sample tissue, which may be forestalled temporarily or indefinitely in order to change the tip of the device to allow a larger or smaller target sample, for example. Also, according to embodiments, the forward cutting tips of the penetration rods may be used, without alteration of their natural shape, attachment or any other modification, to penetrate the tissue segments on approach to the target, and then may be used to surround, immobilize and isolate the tissue specimen. Thereafter, the same penetration rod tips may be used to part-off the specimen at the end of the isolation stage, as well as to augment retrieval of the collected specimen. Having these multiple functions saves valuable cross-sectional area, which in turn, creates a device that is as minimal as possible in outer diameter for entry and penetration to the target site while providing a means to capture and remove a target tissue much larger than that outer diameter. This is clinically significant, since embodiments optimize the ratio so that the clinician and patient can have the best of both worlds.

The manner in which the curved tips deploy around the target tissue is also advantageous. Indeed, the curved tips are configured to deploy around the target tissue without touching the suspect lesion that it is surrounding. In this manner, the clinically significant tissue architecture of the collected specimen is least likely to be disrupted. Again, it has been clearly demonstrated that minimizing tissue artifact and preserving tissue architecture as much as possible leads to a better diagnosis and more favorable postoperative results. The sliding carriage element advantageously provides structure within an upper unit of the device for locating the various internal drive components. Moreover, the ability to move this carriage with its components as a unit gives the operator unique options to vary the captured tissue sample length and volume in real time, intra-procedurally, with a simple mechanical arrangement powered manually or automatically as selected.

Also advantageous are the multiplicity of entry/forward penetration and withdrawal mechanisms; a post-procedural cavity shaping capability, both with the carriage function as well as manually; the ability to approach a target tissue or foreign body head on; the ability to extract maximum volume for a minimum surface area (spherical shape of captured tissue); the ability to bypass structures on the way to a target or avoid structures proximal to a target site; the ability to pre-select the volume of tissue to be excised; the ability to deliver a multiplicity of materials and apparatus to a target site and even within the target when it is immobilized or isolated; the ability to conduct the procedure with image guidance or without it, if necessary; the multiplicity of additional functions and features that may be added to the basic device; the simple, robust, scalable and recyclable structure of the device itself; the safety factors associated with the replaceable upper and lower units of the device; and the ability to change only the device tip between interventional procedures.

Finally, embodiments are highly portable, requiring minimal supporting equipment, especially in battery or mechanical embodiment such as in a wind-up spring powered alternative (not shown) or simple manual operation. Advantageously, embodiments may find widespread application throughout the world for excision biopsy procedures. Other instruments designed for the purpose of tissue biopsy need, by their design limitations, far more adjunct supporting mechanisms, such as external drive systems, fluid management and tissue management systems, as well as separate retrieval-assist systems, all of which are built in or optional features of the present embodiments, but which are not required for operation.

Variations are possible. For example, according to one embodiment, the penetrating rod element(s) that are housed in their loaded delivery tube(s) need not be pointed or have cutting edges to accomplish such a purpose, but may in fact be distally fan-shaped, barbed, webbed or have another configuration configured for isolation or capture of a specific target. The number of penetrating rod elements may vary considerably from one to any number desired for efficiency in capture, isolation and retrieval of a target. Embodiments of the present device may also be curved rather than straight along its longitudinal axis and may still be configured to function properly.

According to one embodiment, a biopsy/excision/isolation device may comprise a multi-tube multiple finger or rod capture and collect component for example, rendering the device potentially suitable to many commercial/industrial applications where handling a variety or single-type material(s) is/are desirable, potentially on a much larger scale than needed in medical biopsy procedures. For example, one embodiment may be adapted for use on a robotic arm for collection and retrieval of samples, whether solid or semi-solid, in remote or dangerous locations. Moreover, due to the lightweight nature of embodiments, it may replace existing capture mechanisms where weight is extremely important, such as for remote planetary rovers. Also, according to one embodiment, the forward distal tip and/or body of the device may be configured to be steerable without loss of any of its functions, which may have uses both within the medical field as well as outside it. Additionally, the length of the barrel assembly portion of such a device may be configured to have most any length, with varying degrees of flexibility, and in a variety of shapes that may find utility in remote applications.

While certain embodiments have been described, these embodiments have been presented by way of example only, and are not intended to limit the scope of the embodiments. Indeed, the novel methods, devices and systems described herein may be embodied in a variety of other forms. Furthermore, various omissions, substitutions and changes in the form of the methods and systems described herein may be made without departing from the spirit of the embodiments. The accompanying claims and their equivalents are intended to cover such forms or modifications as would fall within the scope and spirit of the disclosed embodiments. For example, those skilled in the art will appreciate that in various embodiments, the actual structures may differ from those shown in the figures. Depending on the embodiment, certain of the steps described in the example above may be removed, others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A method, comprising:
   inserting a central tube of a device into tissue to a position adjacent a target tissue portion;
   deploying a plurality of rod elements, radially disposed around the central tube, from and out of a distal end of the device, each of the plurality of rod elements being configured to rotate about its own rotation axis and each comprising a curved and unattached free end portion comprising a leading sharpened edge, such that the curved and unattached free end portions of the deployed rod elements collectively circumscribe a volume of tissue enclosing the target tissue portion and an amount of tissue surrounding the target tissue portion as each of the plurality of rod elements is rotated about its own axis and as the device is rotated;
   immobilizing the target tissue portion within the circumscribed volume of tissue;
   rotating the deployed plurality of rod elements such that the leading sharpened edges thereof cut the circumscribed volume of tissue; and
   parting off the circumscribed volume of tissue from surrounding tissue.

2. The method of claim 1, further comprising delivering a liquid into the volume collectively circumscribed by the curved and unattached free end portions of the deployed rod elements.

3. The method of claim 2, wherein the liquid comprises a lysing agent.

4. The method of claim 1, further comprising retracting the parted-off tissue portion and the amount of tissue surrounding the target tissue.

5. The method of claim 1, further comprising delivering a biologically active material into the volume collectively circumscribed by the curved and unattached free end portions of the deployed rod elements.

6. The method of claim 5, wherein the biologically active material comprises at least one of an implant, a radioactive pellet and a medication.

7. The method of claim 1, further comprising deploying a sleeve over the deployed plurality of rod elements.

8. The method of claim 1, wherein deploying comprises moving each of the plurality of rod elements axially within a respective one of a plurality of tube chambers disposed radially around the central tube.

9. The method of claim 1 wherein parting off comprises completing at least one complete rotation of the plurality of deployed rod elements.

10. A device for cutting tissue, comprising:
    a central tube,
    a plurality of tube chambers radially disposed around the central tube, each comprising a rod element disposed therein, each rod element being configured to rotate about its own rotation axis and comprising a curved and unattached free end portion comprising a leading sharpened edge, the curved and unattached free end portion being biased against an internal surface within the tube chamber to assume a first radius of curvature;
    wherein each of the plurality of rod elements is configured for deployment from and out of its respective tube chamber while rotating about its own axis, the curved and unattached free end portion of each of the plurality of rod elements being configured to assume a second radius of curvature when deployed outside of its respective tube chamber, the second radius of curvature being smaller than the first radius of curvature and wherein the plurality of rod elements, in their deployed state, are configured to be rotated as the device is rotated such that the leading sharpened edges of the curved and unattached free end portions thereof cut and part off a volume of revolution of the tissue.

11. The device of claim 10, wherein each of the plurality of tube chambers comprises a sharpened distal end and wherein the plurality of tube chambers are collectively disposed in a tissue penetrating configuration.

12. The device of claim 10, further comprising a locating wire disposed within the central tube.

13. The device of claim 10, further comprising a locating tube within which the device may be advanced.

14. The device of claim 10, wherein the plurality of rod elements are configured such that the curved and unattached free end portions, upon being deployed from their respective tube chamber, are configured to enclose a spheroidal volume.

15. The device of claim 10, wherein each of the plurality of rod elements is configured to move axially within a respective one of the plurality of tube chambers at least during deployment.

* * * * *